US011142800B2

(12) United States Patent
Ting et al.

(10) Patent No.: US 11,142,800 B2
(45) Date of Patent: Oct. 12, 2021

(54) BIOMARKERS OF CANCER

(71) Applicant: The General Hospital Corporation, Boston, MA (US)

(72) Inventors: David Tsai Ting, Dover, MA (US); Daniel A. Haber, Chestnut Hill, MA (US); Shyamala Maheswaran, Lexington, MA (US); Doron Lipson, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 610 days.

(21) Appl. No.: 15/589,586

(22) Filed: May 8, 2017

(65) Prior Publication Data

US 2017/0356054 A1 Dec. 14, 2017

Related U.S. Application Data

(63) Continuation of application No. 13/877,373, filed as application No. PCT/US2011/055108 on Oct. 6, 2011, now abandoned.

(60) Provisional application No. 61/493,800, filed on Jun. 6, 2011, provisional application No. 61/390,956, filed on Oct. 7, 2010.

(51) Int. Cl.
*C12Q 1/68* (2018.01)
*C12P 19/34* (2006.01)
*C12Q 1/6886* (2018.01)

(52) U.S. Cl.
CPC ..... *C12Q 1/6886* (2013.01); *C12Q 2600/158* (2013.01); *C12Q 2600/178* (2013.01)

(58) Field of Classification Search
CPC ............ C12Q 1/6886; C12Q 2600/158; C12Q 2600/178
See application file for complete search history.

(56) References Cited

U.S. PATENT DOCUMENTS

| 3,687,808 | A | 8/1972 | Merigan et al. |
| 4,458,066 | A | 7/1984 | Caruthers et al. |
| 4,469,863 | A | 9/1984 | Ts'o et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Dinh et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 5,013,830 | A | 5/1991 | Ohtsuka et al. |
| 5,023,243 | A | 6/1991 | Tullis |
| 5,034,506 | A | 7/1991 | Summerton et al. |
| 5,045,694 | A | 9/1991 | Beavis et al. |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,802 | A | 6/1992 | Smith et al. |
| 5,118,937 | A | 6/1992 | Hillenkamp et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer et al. |
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,220,007 | A | 6/1993 | Pederson et al. |
| 5,235,033 | A | 8/1993 | Summerton et al. |
| 5,245,022 | A | 9/1993 | Weis et al. |
| 5,254,469 | A | 10/1993 | Warren et al. |
| 5,256,775 | A | 10/1993 | Froehler |
| 5,258,506 | A | 11/1993 | Urdea et al. |
| 5,262,536 | A | 11/1993 | Hobbs |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,286,717 | A | 2/1994 | Cohen et al. |

(Continued)

FOREIGN PATENT DOCUMENTS

| CN | 1703524 | 11/2005 |
| CN | 101313220 | 11/2008 |

(Continued)

OTHER PUBLICATIONS

US 5,780,277 A, 07/1998, Sheridan et al. (withdrawn)
Horard, B. et al. Epigenetics, 2009; vol. 4 Issue 5, p. 339-350. (Year: 2009).*
Eymery, A. et al. Nucleic Acids Research, 2009, vol. 37, No. 19, p. 6340-6354. (Year: 2009).*
V. Alexiadis et al. Biochimica et Biophysica Acta 1769 (2007) 29-40 (Year: 2007).*
Kikuchi, Y. et al., (2005) Treatment options in the management of ovarian cancer, Expert Opinion on Pharmacotherapy, 6:5, 743-754 (Year: 2005).*

(Continued)

*Primary Examiner* — Stephen T Kapushoc
(74) *Attorney, Agent, or Firm* — Fish & Richardson P.C.

(57) ABSTRACT

Methods for diagnosing cancer based on detecting the presence of increased levels of expression of satellite repeats and/or Line-1.

11 Claims, 8 Drawing Sheets

Specification includes a Sequence Listing.

(56) References Cited

U.S. PATENT DOCUMENTS

| | | |
|---|---|---|
| 5,292,873 A | 3/1994 | Rokita et al. |
| 5,317,098 A | 5/1994 | Shizuya et al. |
| 5,321,131 A | 6/1994 | Agrawal et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Krniec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,652,355 A | 7/1997 | Metelev et al. |
| 5,652,356 A | 7/1997 | Agrawal |
| 5,663,312 A | 9/1997 | Chaturvedula |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,922 A | 12/1997 | Cook |
| 5,714,331 A | 2/1998 | Buchardt et al. |
| 5,716,928 A | 2/1998 | Benet et al. |
| 5,719,060 A | 2/1998 | Hutchens et al. |
| 5,719,262 A | 2/1998 | Buchardt et al. |
| 5,750,692 A | 5/1998 | Cook et al. |
| 5,858,401 A | 1/1999 | Bhalani et al. |
| 6,007,839 A | 12/1999 | Mayhew et al. |
| 6,063,400 A | 5/2000 | Geho et al. |
| 6,225,047 B1 | 5/2001 | Hutchens et al. |
| 6,268,490 B1 | 7/2001 | Imaishi et al. |
| 6,287,860 B1 | 9/2001 | Monia et al. |
| 6,734,291 B2 | 5/2004 | Kochkine et al. |
| 6,770,748 B2 | 8/2004 | Imanishi et al. |
| 6,794,499 B2 | 9/2004 | Wengel et al. |
| 7,033,758 B2 | 4/2006 | Kenny et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,084,125 B2 | 8/2006 | Wengel |
| 7,572,582 B2 | 8/2009 | Wengel et al. |
| 7,709,198 B2 | 5/2010 | Luo et al. |
| 7,741,345 B2 | 6/2010 | Cannizzaro et al. |
| 7,803,541 B2 | 9/2010 | Luo et al. |
| 8,008,449 B2 | 8/2011 | Korman et al. |
| 8,114,681 B2 | 2/2012 | Martin et al. |
| 8,476,246 B2 | 7/2013 | Schlingensiepen et al. |
| 8,591,900 B2 | 11/2013 | Barrett et al. |
| 8,778,906 B2 | 7/2014 | Bondarev et al. |
| 8,790,655 B2 | 7/2014 | Carson et al. |
| 8,795,678 B2 | 8/2014 | Liang et al. |
| 9,073,994 B2 | 7/2015 | Honjo et al. |
| 9,512,446 B1 | 12/2016 | Joung et al. |
| 2002/0042072 A1 | 4/2002 | Meel |
| 2003/0165499 A1 | 9/2003 | Chu et al. |
| 2004/0028670 A1 | 2/2004 | Carlson et al. |
| 2004/0120948 A1 | 6/2004 | Mikayama et al. |
| 2005/0119201 A1 | 6/2005 | Selker et al. |
| 2006/0115806 A1 | 6/2006 | McDonald |
| 2006/0263769 A1 | 11/2006 | Luo et al. |
| 2007/0021442 A1 | 1/2007 | Saggar et al. |
| 2007/0088015 A1 | 4/2007 | Silva et al. |
| 2007/0148163 A1 | 6/2007 | Takahashi et al. |
| 2007/0191294 A1 | 8/2007 | Elmen et al. |
| 2008/0249039 A1 | 10/2008 | Elmen et al. |
| 2009/0068660 A1 | 3/2009 | Hoon et al. |
| 2009/0143326 A1 | 6/2009 | Obad et al. |
| 2009/0162319 A1 | 6/2009 | Shanginian et al. |
| 2009/0181914 A1 | 7/2009 | Rosenbohm et al. |
| 2009/0280479 A1 | 11/2009 | Hoon et al. |
| 2009/0298916 A1 | 12/2009 | Kauppinen et al. |
| 2010/0004320 A1 | 1/2010 | Elmen et al. |
| 2010/0035968 A1 | 2/2010 | Rasmussen et al. |
| 2010/0234451 A1 | 9/2010 | Worm |
| 2010/0249052 A1 | 9/2010 | Benson et al. |
| 2010/0261175 A1 | 10/2010 | Rasmussen et al. |
| 2010/0267018 A1 | 10/2010 | Wengel et al. |
| 2010/0317718 A1 | 12/2010 | Marcusson et al. |
| 2011/0218170 A1 | 9/2011 | Thottassery et al. |
| 2011/0271358 A1 | 11/2011 | Freeman et al. |
| 2012/0003648 A1 | 1/2012 | Ma et al. |
| 2012/0004132 A1 | 1/2012 | Zhang et al. |
| 2012/0029192 A1 | 2/2012 | Jones et al. |
| 2012/0052498 A1 | 3/2012 | Nguyen et al. |
| 2012/0053213 A1 | 3/2012 | Xie et al. |
| 2012/0071343 A1 | 3/2012 | Ma et al. |
| 2012/0100540 A1 | 4/2012 | Wu et al. |
| 2012/0135950 A1 | 5/2012 | Kaplan et al. |
| 2012/0172246 A1 | 7/2012 | Nguyen et al. |
| 2012/0214152 A1 | 8/2012 | Ma et al. |
| 2012/0225894 A1 | 9/2012 | Giradet et al. |
| 2012/0321637 A1 | 12/2012 | Dong et al. |
| 2013/0011405 A1 | 1/2013 | Long et al. |

(56) References Cited

U.S. PATENT DOCUMENTS

| | | |
|---|---|---|
| 2013/0023433 A1 | 1/2013 | Luo et al. |
| 2013/0171621 A1 | 7/2013 | Luo et al. |
| 2013/0296382 A1 | 11/2013 | Burch et al. |
| 2014/0031250 A1 | 1/2014 | Ting et al. |
| 2014/0287956 A1 | 9/2014 | Ting et al. |
| 2014/0295557 A1 | 10/2014 | Joung et al. |
| 2015/0105351 A1 | 4/2015 | Jorgensen et al. |
| 2015/0246067 A1 | 9/2015 | Kaplan et al. |
| 2015/0258068 A1 | 9/2015 | Gold et al. |
| 2015/0290235 A1 | 10/2015 | Gros et al. |
| 2016/0000796 A1 | 1/2016 | Takaori et al. |
| 2016/0145255 A1 | 5/2016 | Arrington et al. |
| 2017/0049909 A1 | 2/2017 | Cullen et al. |
| 2017/0058033 A1 | 3/2017 | Ludwig et al. |
| 2017/0198288 A1 | 7/2017 | Ting et al. |
| 2017/0267667 A1 | 9/2017 | Cushman et al. |
| 2017/0356054 A1 | 12/2017 | Ting et al. |

FOREIGN PATENT DOCUMENTS

| | | |
|---|---|---|
| EP | 1961825 | 8/2008 |
| EP | 1732569 B1 | 10/2009 |
| EP | 2119784 | 11/2009 |
| EP | 1871391 B1 | 12/2011 |
| WO | WO 2000/035473 | 6/2000 |
| WO | WO 2002/088186 | 11/2002 |
| WO | WO 2004/031412 | 4/2004 |
| WO | WO 2004/035819 | 4/2004 |
| WO | WO 2004/069174 | 8/2004 |
| WO | WO 2005/069880 | 8/2005 |
| WO | WO 2005/072748 | 8/2005 |
| WO | WO 2006/103562 | 10/2006 |
| WO | WO 2006/108048 | 10/2006 |
| WO | WO 2007/124299 | 11/2007 |
| WO | WO 2008/030605 | 3/2008 |
| WO | WO 2008/083634 | 7/2008 |
| WO | WO 2009/038756 | 3/2009 |
| WO | WO 2009/090639 | 7/2009 |
| WO | WO 2009/114547 | 9/2009 |
| WO | WO 2010/135690 | 11/2010 |
| WO | WO 2011/123489 | 10/2011 |
| WO | WO 2011/127219 | 10/2011 |
| WO | WO 2012/048113 | 4/2012 |
| WO | WO 2012/111762 | 8/2012 |
| WO | WO 2012/149356 | 11/2012 |
| WO | WO 2013/035114 | 3/2013 |
| WO | WO 2013/063035 | 5/2013 |
| WO | WO 2013/079174 | 6/2013 |
| WO | WO 2013/173223 | 11/2013 |
| WO | WO 2014/070934 | 5/2014 |
| WO | WO 2014/195852 | 12/2014 |
| WO | WO 2015/200697 | 12/2015 |
| WO | WO 2016/007235 | 1/2016 |
| WO | WO 2016/061142 | 4/2016 |
| WO | WO 2018/022480 | 2/2018 |

OTHER PUBLICATIONS

Resnick, K.E. et al. Gynecologic Oncology 112 (2009) 55-59 (Year: 2009).*
International Preliminary Report on Patentability in International Application No. PCT/US2011/055108, dated Apr. 9, 2013, 8 pages.
International Preliminary Report on Patentability in International Application No. PCT/US2012/061576, 6 pages.
International Search Report and Written Opinion dated Feb. 7, 2013 for corresponding application PCT/US2012/061576, 7 pages.
International Search Report and Written Opinion dated Jun. 1, 2012 for corresponding application PCT/US2011/055108, 12 pages.
Office Action in CN Application No. 201180058942.X, dated Jan. 30, 2015, 12 pages.
Office Action in CN Application No. 201180058942.X, dated Jun. 9, 2014, 12 pages.
Office Action in CN Application No. 201180058942.X, dated Aug. 17, 2015, 13 pages.
Office Action in CN Application No. 201280063658.6, dated Apr. 3, 2015, 10 pages.
Office Action in CN Application No. 201280063658.6, dated Sep. 15, 2015, 6 pages.
Office Action in CN Application No. 201180058942.X, dated Feb. 24, 2016, 29 pages (English Translation).
Office Action in EP Application No. 11831599.3, dated Feb. 23, 2016, 5 pages.
Office Action in GB Application No. GB 1409192.0, dated Oct. 2, 2014, 3 page.
Office Action in GB Application No. GB 1409192.0, dated Jan. 8, 2015, 3 pages.
Office Action in GB Application No. GB 1409192.0, dated Apr. 13, 2015, 1 page.
Office Action in GB Application No. GB 1409192.0, dated Feb. 2, 2016, 1 page.
Office Action in JP Application No. JP 2014538904, dated Feb. 9, 2016, 52 pages (with English translation).
Supplementary European Search Report dated Feb. 7, 2014 for corresponding application EP11831599.3.
Partial Supplementary European Search Report in Application No. 12843478.4, dated Jun. 3, 2015, 6 pages.
Extended European Search Report in European Application No. 12843478.4, dated Sep. 22, 2015, 10 pages.
U.S. Final Office Action in U.S. Appl. No. 14/353,708, dated Jan. 22, 2016, 50 pages.
U.S. Non-Final Office Action in U.S. Appl. No. 14/353,708, dated Aug. 14, 2015, 59 pages.
U.S. Non-Final Office Action in U.S. Appl. No. 13/877,373, dated Dec. 21, 2015, 23 pages.
U.S. Final Office Action in U.S. Appl. No. 13/877,373, dated Jun. 8, 2016, 19 pages.
Alexiadis et al., "RNAPol-ChIP Analysis of Transcription from FSHD-Linked Tandem Repeats and Satellite DNA," Biochim. Biophys. Acta., Jan. 2007, 1769:29-40.
Aravin et al., "The Piwi-piRNA pathway provides an adaptive defense in the transposon arms race," Science, 318(5851):761-4 (Nov. 2, 2007).
Babushok and Kazazian, "Progress in understanding the biology of the human mutagen Line-1,", Hum Mutat., 28(6):527-39 (2007).
Bailey et al., "Molecular evidence for a relationship between Line-1 elements and X chromosome inactivation: the Lyon repeat hypothesis," Proc Natl Acad Sci USA, 97(12):6634-9 (Jun. 6, 2000).
Bardeesy et al., "Both p16(Ink4a) and the p19(Arf)-p53 pathway constrain progression of pancreatic adenocarcinoma in the mouse," Proc Natl Acad Sci USA, 103(15)5947-52 (Apr. 11, 2006).
Belancio et al., "Line dancing in the human genome: transposable elements and disease," Genome Med., 1:97-97.8 (2009).
Benner et al., "Evolution, language and analogy in functional genomics," Trends Genet. Jul. 2001;17(7):414-8.
Berretta and Morillon, "Pervasive transcription constitutes a new level of eukaryotic genome regulation," EMBO Rep., 10(9):973-82 (Sep. 2009).
Bodmer et al., "Disruption of a novel gene, DIRC3, and expression of DIRC3-HSPBAP1 fusion transcripts in a case of familial renal cell cancer and t(2;3)(q35;q21),"Genes Chromosomes Cancer, 38(2):107-16 (Oct. 2003).
Bouzinba-Segard et al., "Accumulation of small murine minor satellite transcripts leads to impaired centromeric architecture and function," PNAS, 103(23):8709-8714 (Jun. 2006).
Brouha et al., "Hot L1s account for the bulk of retrotransposition in the human population," Proc Natl Acad Sci USA, 100(9):5280-5 (2003).
Carone et al., "A new class of retroviral and satellite encoded small RNAs emanates from mammalian centromeres," Chromosoma, 118(1):113-25 (Feb. 2009).
Chen et al., "The HSP90 family of genes in the human genome: Insights into their divergence and evolution," Genomics, Academic Press, Dec. 2005, pp. 627-637.
Cheung et al., "Natural variation in human gene expression assessed in lymphoblastoid cells," Nat Genet. Mar. 2003;33(3):422-5.

(56) References Cited

OTHER PUBLICATIONS

Choi et al., "Hypomethylation of Line-1 and Alu in well-differentiated neuroendocrine (pancreatic endocrine tumors and carcinoid tumors),"Modern Pathology, 2007, 20: 802-810.
Cindolo et al., "Neuroendocrine differentiation in prostate cancer: from lab to bedside," Urol Int., 79(4):287-96 (2007).
Cloos et al., "Erasing the methyl mark: histone demethylases at the center of cellular differentiation and disease," Genes Dev., 22(9):1115-40 (2008).
Cohen et al., "Mouse major satellite DNA is prone to eccDNA formation via DNA Ligase IV-dependent pathway," Oncogene, 25:4515-4524 (2006).
Cohen et al., "Small polydispersed circular DNA (spcDNA) in human cells: association with genomic instability," Oncogene, 14:977-985 (1997).
Comuzzie et al., "Novel Genetic Loci Identified for the Pathophysiology of Childhood Obesity in the Hispanic Population," PLoS One, 2012, 7(12): e51954.
Cordaux and Batzer, "The impact of retrotransposons on human genome evolution," Nat Rev Genet., 10(10):691-703 (2009) (Author Manuscript).
Daskalos et al., "Hypomethylation of retrotransposable elements correlates with genomic instability in non-small cell lung cancer," Int J Cancer, 124:81-87 (2009).
Dennis, Jr. et al., "DAVID: Database for Annotation, Visualization, and Integrated Discovery," Genome Biol., 4(5):P3 (2003).
Enukashvily et al., "Human chromosome 1 satellite 3 DNA is decondensed, demethylated and transcribed in senescent cells and in A431 epithelial carcinoma cells," Cytogenet Genome Res., 2007, 118(1):42-54.
Florl et al., "DNA methylation and expression of Line-1 and HERV-K provirus sequences in urothelial and renal cell carcinomas," British Journal of Cancer, 1999, 80(9):1312-1321.
Frescas et al., "JHDM1B/FBXL10 is a nucleolar protein that represses transcription of ribosomal RNA genes," Nature, 450(7167):309-13 (Nov. 8, 2007).
Fukagawa et al., "Dicer is essential for formation of the heterochromatin structure in vertebrate cells," Nature Cell Biol., 6(8):784-791 & supplementary info pp. 1-4 (Aug. 2004).
Gibb et al., "Human Cancer Long Non-Coding RNA Transcriptomes," PLoS One, 6(10):e25915, 10 pages (Oct. 3, 2011).
Gibb et al., "The functional role of long non-coding RNA in human carcinomas," Mole Cancer, 10(1):38, 17 pages (Apr. 13, 2011).
Greenbaum et al., "Comparing protein abundance and mRNA expression levels on a genomic scale," Genome Biology 2003, vol. 4, article 117, pp. 1-8.
Guenatri et al., "Mouse centric and pericentric satellite repeats form distinct functional heterochromatin," J Cell Biol., 166(40:493-505 (Aug. 16, 2004).
Gupta et al., "Long non-coding RNA Hotair reprograms chromatin state to promote cancer metastasis," Nature, 464(7291):1071-1076 (2010).
Halic and Moazed, "Dicer-independent primal RNAs trigger RNAi and heterochromatin formation," Cell, 140(4):504-16 (Feb. 19, 2010) (Author Manuscript).
Harris et al., "Association of Nuclear Localization of a Long Interspersed Nuclear Element-1 Protein in Breast Tumors with Poor Prognostic Outcomes," Genes Cancer, 1(2):115-124 (2010).
Hu, et al. "Comparative analysis of protein-coding genes and long non-coding RNAs of prostate cancer between Caucasian and Chinese populations." Systems Biology (ISB), 2012 IEEE 6th International Conference on. IEEE, 2012, 291-296.
Huang et al., "Systematic and integrative analysis of large gene lists using DAVID bioinformatics resources," Nat Protoc., 4(1):44-57 (2009).
Jacquier, "The complex eukaryotic transcriptome: unexpected pervasive transcription and novel small RNAs," Nat Rev Genet., 10(12):833-44 (Dec. 2009).
Jurka et al., "Repbase Update, a database of eukaryotic repetitive elements," Cytogenet Genome Res., 110(1-4):462-7 (2005).
Kanellopoulou et al., "Dicer-deficient mouse embryonic stem cells are defective in differentiation and centromeric silencing," Genes Dev., 19:489-501, (2005).
Karolchik et al., "The UCSC Table Browser data retrieval tool," Nucleic Acids Res., 32:D493-6 (Jan. 1, 2004).
Kishikawa, "Non-coding Satellite RNAs are Highly Expressed in Cancer Adjacent Lesions of Human Pancreatic Carcinoma and May Promote Oncogenesis," Cancer Research 73(8, Supp. 1) Abstract 5291 (2013).
Kuwabara et al., "Wnt-mediated activation of NeuroD1 and retro-elements during adult neurogenesis," Nat Neurosci., 12(9):1097-105 (Sep. 2009) (Author Manuscript).
Lipson et al., "Quantification of the yeast transcriptome by single-molecule sequencing," Nat Biotechnol., 27(7):652-8 (Jul. 2009).
Maheswaran et al., "Detection of mutations in EGFR in circulating lung-cancer cells," N Engl J Med., 359(4):366-77 (Jul. 24, 2008).
Martens et al., "The profile of repeat-associated histone lysine methylation states in the mouse epigenome," EMBO J., 24(4):800-12 (Feb. 23, 2005).
MGC4836 (http://www.ncbi.nlm.nih.gov/pubmed/?term=mgc4836 downloaded Aug. 6, 2015), 1 page.
Montoya-Durango et al., "Epigenetic control of mammalian Line-1 retrotransposon by retinoblastoma proteins," Mutat Res., 665(1-2):20-8 (Jun. 1, 2009) (Author Manuscript).
Nagrath et al., "Isolation of rare circulating tumour cells in cancer patients by microchip technology," Nature, 450(7173):1235-9 (Dec. 20, 2007).
NCBI reference sequence NR_003132.1 (http://www.ncbi.nlm.nih.gov/nuccore/nr_003132.1, downloaded Aug. 5, 2015), 1 page.
Okada et al., "CENP-B controls centromere formation depending on the chromatin context," Cell, 131(7):1287-300 (Dec. 28, 2007).
Ozsolak et al., "Direct RNA sequencing," Nature. Oct. 8, 2009;461(7265):814-8.
Paik et al., "A multigene assay to predict recurrence of tamoxifen-treated, node-negative breast cancer," N Engl J Med. Dec. 30, 2004;351(27):2817-26.
Player et al., "Single-copy Gene Detection Using Branched DNA (bDNA) in Situ Hybridization,"The Journal of Histochemisrty & Cytochemistry, 2001, 49(5): 603-611.
Pushkarev et al., "Single-molecule sequencing of an individual human genome," Nat Biotech., 27(9):847-50 (2009).
Riehle et al., "A Cryptic Subgroup of Anopheles gambiae Is Highly Susceptible to Human Malaria Parasites," Science, Feb. 4, 2011.
Roman-Gomez et al., "Promoter hypomethylation of the Line-1 retrotransposable elements activates sense/antisense transcription and marks the progression of chronic myeloid leukemia," Oncogene, 24:7213-7223 (2005).
Saito-Hisaminato et al., "Genome-wide profiling of gene expression in 29 normal human tissues with a cDNA microarray," DNA Res. Apr. 30, 2002;9(2):35-45.
Sciencemag.com [online]. "Supporting Online Material for Aberrant Overexpression of Satellite Repeats in Pancreatic and Other Epithelial Cancers," Jan. 13, 2011. www.sciencemag.org/cgi/content/full/science.1200801/DC1, 40 pages.
Shaffer et al., "Genome-wide association study of periodontal health measured by probing depth in adults ages 18-49 years," G3 (Bethesda), Feb. 19, 2014, 4(2):307-14.
Sharma, "Clinical practice. Barrett's esophagus," N Engl J Med., 24; 361(26):2548-56 (2009) Erratum in: N Engl J Med., 362(15):1450 (Apr. 2010).
Stott et al., "Isolation of circulating tumor cells using a microvortex-generating herringbone-chip," Proc Natl Acad Sci USA, 107(43):18392-18397 (2010).
Swergold, "Identification, characterization, and cell specificity of a human Line-1 promoter,"Mol Cell Biol., 10(12):6718-29 (1990).
Sun et al., "Identification of differentially expressed genes in human lung squamous cell carcinoma using suppression subtractive hybridization," Cancer Letters, 2004, 212:83-93.
Tahira et al., "Long noncoding intronic RNAs are Differentially Expressed in Primary and Metastatic Pancreatic Cancer," Molecular Cancer 10:141 (2011).
Tezel et al., "Neuroendocrine-like differentiation in patients with pancreatic carcinoma," Cancer, 89(11):2230-6 (Dec. 1, 2000).

(56) References Cited

OTHER PUBLICATIONS

Ting et al., "Aberrant overexpression of satellite repeats in pancreatic and other epithelial cancers," Science, 331(6017):593-596 (Feb. 4, 2011).
Ugarkovic, "Functional elements residing within satellite DNAs," EMBO Rep., 6(11):1035-9 (Nov. 2005).
Valgardsdottir et al., "Transcription of Satellite III non-coding RNAs is a general stress response in human cells," Nucleic Acids Res., 36(2):423-434 (2008).
Wolf et al, "Heat shock protein 70 is required for optimal liver regeneration after partial hepatectomy in mice," Liver Transplantation 20.3 (2014): 376-385.
Yano et al., "Expression and roles of heat shock proteins in human breast cancer," Jpn J Cancer Res. Sep. 1996;87(9):908-15.
Yonezawa et al., "MUC2 gene expression is found in noninvasive tumors but not in invasive tumors of the pancreas and liver: Its close relationship with prognosis of the patients," Human Pathology, Mar. 1997, 28: 344-352.
European Office Action in European Application No. 12843478.4, dated Sep. 2, 2016, 8 pages.
Sander "Genetic analysis reveals that PAX6 is required for normal transcription of pancreatic hormone genes and islet development," Genes & Development, 1997, 11: 1662-1673.
Blast®, blastn suite, RID-OCDSEVUK016 (https://blast.ncbi.nlm.nih.gov/Blast.cgi, downloaded Oct. 18, 2016, 221 pages.
Japanese Office Action in Japanese Application No. 2014-538904, dated Dec. 13, 2016, 9 pages (with English translation).
European Office Action in European Application No. 11831599.3, dated Mar. 10, 2017, 6 pages.
Chinese Office Action in Application No. 201180058942.X, dated Feb. 7, 2017, 22 pages (with English translation).
European Office Action in European Application No. 12843478.4, dated May 10, 2017, 6 pages.
Abudayyeh et al., "RNA targeting with CRISPR—Cas13," Nature, Oct. 2017, 550(7675):280-284.
Adams et al., "Hindered dialkylamino nucleoside phosphite reagents in the synthesis of two DNA 51-mers," J. Am. Chem. Soc., Feb. 1983, 105(3):661-663.
Ahmadian et al., "Single-nucleotide polymorphism analysis by pyrosequencing," Anal. Biochem., 2000, 280(1):103-110.
Alexandrescu et al., "Immunotherapy for melanoma: current status and perspectives," J. Immunother., Jul. 2010, 33(6): 570-590.
Al-Muhammed et al., "In-vivo studies on dexamethasone sodium phosphate liposomes," J. Microencapsul., Jan. 1996, 13(3):293-306.
Altschul et al., "Basic local alignment search tool," J. Mol. Biol., Oct. 1990, 215(3):403-410.
Asokan et al., "The AAV vector toolkit: poised at the clinical crossroads," Molecular Therapy, Apr. 2012, 20(4):699-708.
Azzalin et al., "Telomeric Repeat—Containing RNA and RNA Surveillance Factors at Mammalian Chromosome Ends," Science, Nov. 2007, 318: 798-801.
Badal et al., "Transcriptional dissection of melanoma identifies a high-risk subtype underlying TP53 family genes and epigenome deregulation," JCI Insight, May 2017, 2(9):e92102, 16 pages.
Bartel et al., "Isolation of new ribozymes from a large pool of random sequences [see comment]," Sep. 1993, Science, 261(5127):1411-1418.
Bass et al., "Genomic sequencing of colorectal adenocarcinomas identifies a recurrent VTI1A-TCF7L2 fusion," Nat Genet, Sep. 2011, 43: 964-968.
Beaucage & Caruthers, "Deoxynucleoside phosphoramidites—a new class of key intermediates for deoxypolynucleotide synthesis," Jan. 1981, Tetra. Lett., 22(20):1859-1862.
Beaudry et al., "Directed evolution of an RNA enzyme," Science, Jul. 1992, 257(5070):635-641.
Beletskii et al., "PNA interference mapping demonstrates functional domains in the noncoding RNA Xist," Proc. Natl. Acad. Sci. U.S.A., Aug. 2001, 98(16):9215-9220.
Belousov et al., "Sequence-specific targeting and covalent modification of human genomic DNA," Nucleic Acids Res., Sep. 1997, 25(17):3440-3444.
Benton & Davis, "Screening lambdagt recombinant clones by hybridization to single plaques in situ," Science, Apr. 1977, 196(4286):180-182.
Berezhnoy et al., "A clinically useful approach to enhance immunological memory and antitumor immunity," Oncoimmunology, 2014, 3:e28811, 4 pages.
Bernard & Wittwer., "Real-Time PCR Technology for Cancer Diagnostics," Clin. Chem., 2002, 48(8):1178-1185.
Bersani et al., "Pericentromeric satellite repeat expansions through RNA-derived DNA intermediates in cancer," PNAS, Nov. 2015, 112: 15148-15153.
Bianchi et al., "A serum circulating miRNA diagnostic test to identify asymptomatic high-risk individuals with early stage lung cancer," EMBO Mol. Med., Aug. 2011, 3(8):495-503.
Bierhoff et al., "Noisy silence: non-coding RNA and heterochromatin formation at repetitive elements," Epigenetics, Jan. 2014, 9: 53-61.
Black et al., "KDM4A Lysine Demethylase Induces Site-Specific Copy Gain and Rereplication of Regions Amplified in Tumors," Cell, Aug. 2013, 154: 541-555.
Blikstad et al., "Evolution of human endogenous retroviral sequences: a conceptual account," Cell. Mol. Life Sci., Nov. 2008, 65(21):3348-3365.
Bouaoun et al., "TP53 Variations in Human Cancers: New Lessons from the IARC TP53 Database and Genomics Data.," Hum. Mutat. Jul. 2016, 37(9):865-876, 38 pages.
Braasch et al., "Novel Antisense and Peptide Nucleic Acid Strategies for Controlling Gene Expression," Biochemistry, Mar. 2002, 41(14):4503-4510.
Breaker et al., "Inventing and improving ribozyme function: rational design versus iterative selection methods," TIBTECH, Jul. 1994, 12(7):268-275.
Breaker, "Are engineered proteins getting competition from RNA?," Curr. Op. Biotech, Aug. 1996, 7(4):442-448.
Brody et al., "High-content affinity-based proteomics: unlocking protein biomarker discovery." Expert Rev. Mol. Diagn., Nov. 2010, 10(8):1013-1022.
Brophy et al., "Bioavailability of oral dexamethasone during high dose steroid therapy in neurological patients," Eur. J. Clin. Pharmacol., 1983 24(1):103-108.
Brown et al., "[8] Chemical synthesis and cloning of a tyrosine tRNA gene," Meth. Enzymol., Jan. 1979, 68:109-151.
Brummelkamp et al., "A system for stable expression of short interfering RNAs in mammalian cells," Science, Apr. 2002, 296(567):550-553.
Canales et al., "Evaluation of DNA microarray results with quantitative gene expression platforms," Nat. Biotechnol., Sep. 2006, 24(9):1115-1122.
Chen et al., "Elements of cancer immunity and the cancer-immune set point," Nature, Jan. 2017, 541(7637):321-330.
Cheng et al., "Plasma membrane associated transcription of cytoplasmic DNA," PNAS, Jul. 2012, 109: 10827-10831.
Chiappinelli et al., "Inhibiting DNA methylation causes an interferon response in cancer via dsRNA including endogenous retroviruses," Cell, Aug. 2015, 162(5):974-986.
Chonn & Cullis., "Recent advances in liposomal drug-delivery systems," Curr. Opin. Biotechnol., Dec. 1995, 6(6):698-708.
Christoffersen & Marr, "Ribozymes as human therapeutic agents," J. Med. Chem., Jun. 1995, 38(12):2023-2037.
Chu et al., "Genomic Maps of Long Noncoding RNA Occupancy Reveal Principles of RNA-Chromatin Interactions," Mol Cell, Nov. 2011, 44: 667-678.
Cieslewicz et al., "Targeted delivery of proapoptotic peptides to tumor-associated macrophages improves survival," Proc. Natl. Acad. Sci. U.S.A., Oct. 2016, 110(40):15919-1524.
Coffman et al., "Endothelin receptor-A is required for the recruitment of antitumor T cells and modulates chemotherapy induction of cancer stem cells." Cancer Biol. Ther., Feb. 2013, 14(2): 184-192.
Cong et al., "Multiplex genome engineering using CRISPR/Cas systems," Science, Feb. 2013, 339(6121):819-823.

(56) References Cited

OTHER PUBLICATIONS

Crooke et al., "Pharmacokinetic properties of several novel oligonucleotide analogs in mice," J. Pharmacol. Exp. Ther., May 1996, 277(2):923-937.
Crosetto et al., "Nucleotide-resolution DNA double-strand break mapping by next-generation sequencing," Nat Methods, Apr. 2013, 10: 361-365.
Day et al., "Estimating enrichment of repetitive elements from high-throughput sequence data," Genome Biol, Jun. 2010, 11: R69.
Debatin., "Chronic lymphocytic leukemia: keeping cell death at bay," Cell, Jun. 2007, 129(5): 853-855.
Desai et al., "Diverse repetitive element RNA expression defines epigenetic and immunologic features of colon cancer," JCI Insight, Feb. 2017, 2(3):e91078.
Diehl et al., "BEAMing: single-molecule PCR on microparticles in water-in-oil emulsions," Nat. Methods, Jul. 2006, 3:551-559.
Dunn et al., "Interferons, immunity and cancer immunoediting," Nat. Rev. Immunol., Nov. 2006, 6:836-848.
Eggermont et al., "Anti—CTLA-4 antibody adjuvant therapy in melanoma," Semin Oncol., Oct. 2010, 37(5): 455-459.
Ekins and Chu., "Microarrays: their origins and applications," Trends in Biotechnology, Jun. 1999, 17:217-218.
Englisch et al., "Chemically modified oligonucleotides as probes and inhibitors," Angewandle Chemie, International Edition, Jun. 1991, 30(6):613-629.
Escamilla-Tilch et al., "The interplay between pathogen-associated and danger-associated molecular patterns: an inflammatory code in cancer?." Immunol. Cell. Biol., 2013, 91(10): 601-610.
Esvelt et al., "Orthogonal Cas9 proteins for RNA-guided gene regulation and editing," Nat. Methods, Nov. 2013, 10(11):1116-1121.
Extended European Search Report in Application No. 15811533.7, dated Jan. 8, 2018, 7 pages.
Eyles et al., "Oral delivery and fate of poly (lactic acid) microsphere-encapsulated interferon in rats," J. Pharm. Pharmacol., Jul. 1997, 49(7):669-674.
Eymery et al., "A transcriptomic analysis of human centromeric and pericentric sequences in normal and tumor cells," Nucleic Acids Res, 2009, 37: 6340-6354.
Eymery et al., "The secret message of heterochromatin new insights into the mechanisms and function of centromeric and pericentric repeat sequence transcription," Int J Dev Biol, 2009, 53: 259-268.
Fagerlund et al., "The Cpf1 CRISPR-Cas protein expands genome-editing tools," Genome Biol., Dec. 2015, 16(1):251, 3 pages.
Flotte et al., "Expression of the cystic fibrosis transmembrane conductance regulator from a novel adeno-associated virus promoter," J. Biol. Chem., Feb. 1993, 268(5):3781-3790.
Fonfara et al., "Phylogeny of Cas9 determines functional exchangeability of dual-RNA and Cas9 among orthologous type II CRISPR-Cas systems," Nucleic Acids Res., Feb. 2014, 42(4):2577-2590.
Fotherby., "Bioavailability of orally administered sex steroids used in oral contraception and hormone replacement therapy." Contraception, Aug. 1996, 54(2):59-69.
Frenkel et al., "7, 12-dimethylbenz [a] anthracene induces oxidative DNA modification in vivo," Free Radic. Biol. Med., Sep. 1995, 19(3):373-380.
Fu et al., "Improving CRISPR-Cas nuclease specificity using truncated guide RNAs," Nat. Biotechnol., Mar. 2014, 32(3):279-284.
Galluzi et al., "Trial Watch: Experimental Toll-like receptor agonists for cancer therapy," Oncoimmunol., Aug. 2012, 1(5): 699-716, 18 pages.
Ganesan and Bakhshi., "Systemic therapy for melanoma." Natl. Med. J. India, Jan. 2010, 23(1):21-27.
Gao et al., "Controlled release of a contraceptive steroid from biodegradable and injectable gel formulations: in vitro evaluation," Pharm. Res., Jun. 1995, 12(6):857-863.
Garcia-Manero., "Demethylating agents in myeloid malignancies," Curr. Opin. Oncol., Nov. 2008, 20(6):705-710.
Gebeyehu et al., "Novel biotinylated nucleotide-analogs for labeling and colorimetric detection of DNA," Nucl. Acids Res., Jun. 1987 15(11):4513-4534.
GenBank Accession No. CAB56603.1, "pol protein [Human endogenous retrovirus K]," Apr. 18, 2005, 2 pages.
GenBank Accession No. WP_051666128.1, "Type V CRISPR-associated protein Cpf1 [Lachnospiraceae bacterium ND2006]," Oct. 1, 2015, 1 pages.
GenBank Reference No. Y.18890.1 "Human endogenous retrovirus type K (HERV-K), gag, pol and env genes," Apr. 18, 2005, 4 pages.
Gilbert et al., "CRISPR-mediated modular RNA-guided regulation of transcription in eukaryotes," Cell, Jul. 2013, 154(2):442-451.
Golan et al., "Human Endogenous Retrovirus (HERV-K) Reverse Transcriptase as a Breast Cancer Prognostic Marker," Neoplasia, Jun. 2008, 10(6):521-533.
Golovina and Vonderheide., "Regulatory T cells: overcoming suppression of T-cell immunity," Cancer J., Aug. 2010, 16(4):342-347.
Grunstein & Hogness, "Colony hybridization: a method for the isolation of cloned DNAs that contain a specific gene," Proc. Natl. Acad. Sci. USA, Oct. 1975, 72(10):3961-3965.
Guo et al., "Interleukin-6 signaling pathway in targeted therapy for cancer." Cancer Treat Rev., Nov. 2012, 38(7):904-910.
Hidalgo-Aragones et al., "Pharmacokinetics of oestrone-3-O-sulphamate," (1996) J. Steroid Biochem. Mol. Biol. Aug. 1996, 58:611-617.
Jeanpierre, "Human satellites 2 and 3," Ann Genet, 1994, 37: 163-171.
Jiang et al., "A molecular view of plant centromeres," Trends Plant Sci, Dec. 2003, 8: 570-575.
Johnson et al., "Permeation of Steroids through Human Skin," J. Pharm. Sci., Sep. 1995, 84(9):1144-1146.
Kim and Bae., "Histone deacetylase inhibitors: molecular mechanisms of action and clinical trials as anti-cancer drugs," Am. J. Transl. Res., Feb. 2011, 3(2):166-179.
Kim et al., "Automated heart-type fatty acid-binding protein assay for the early diagnosis of acute myocardial infarction," Am. J. Clin. Pathol., Jul. 2010, 134(1):157-162.
Klinke., "A multiscale systems perspective on cancer, immunotherapy, and Interleukin-12." Mol. Cancer., Dec. 2010, 9(1): 242.
Krüger et al., "Immune based therapies in cancer,"Histol Histopathol., Jun. 2007, 22(6): 687-696.
Kususda et al., "Clusterin inhibition using OGX-011 synergistically enhances antitumour activity of sorafenib in a human renal cell carcinoma model," British Journal of Cancer, Jun. 2012, 106: 1945-1952.
Lander et al., "Initial sequencing and analysis of the human genome," Nature, Feb. 2001, 409: 8360-921.
Lange, "T-loops and the origin of telomeres," Nat Rev Mol Cell Biol, Apr. 2004, 5: 323-329.
Lee & Margolin., "Cytokines in cancer immunotherapy," Cancers, Oct. 2011, 3(4):3856-3893.
Lee et al., "Landscape of Somatic Retrotransposition in Human Cancers," Science, Aug. 2012, 337: 967-971.
Leonova et al., "p53 cooperates with DNA methylation and a suicidal interferon response to maintain epigenetic silencing of repeats and noncoding RNAs," Proc. Natl. Acad. Sci. USA., Jan. 2013, 110(1):E89-98.
Linton et al., "Microarray gene expression analysis of fixed archival tissue permits molecular classification and identification of potential therapeutic targets in diffuse large B-cell lymphoma," J. Mol. Diagn., May 2012, 14(3): 223-32.
Llorente et al., "Clinical and biologic effects of anti—interleukin-10 monoclonal antibody administration in systemic lupus erythematosus," Arthritis & Rheumatism, Aug. 2000, 43(8):1790-1800.
Lu et al., "Polysaccharide krestin is a novel TLR2 agonist that mediates inhibition of tumor growth via stimulation of CD8 T cells and NK cells," Clin. Cancer Res., Jan. 2011, 17(1):67-76.
Luo et al., "Targeting tumor-associated macrophages as a novel strategy against breast cancer," J. Clin. Invest., Aug. 2006, 116(8):2132-2141.
MacBeath and Schreiber., "Printing proteins as microarrays for high-throughput function determination.," Science, Sep. 2000, 289(5485):1760-1763.

(56) References Cited

OTHER PUBLICATIONS

Maida et al., "An RNA dependent RNA polymerase formed by hTERT and the RNase MRP RNA," Nature, Sep. 2009, 461: 230-235.
Manjili and Butler, "Immune regulatory function of tregs," Immunol Invest., Nov. 2016, 45(8):759-766.
Martinez and Blasco, "Telomeric and extra-telomeric roles for telomerase and the telomere-binding proteins," Nat Rev Cancer, 2011, 11: 161-176.
Martinez et al., "Centromere fission, not telomere erosion, triggers chromosomal instability in human carcinomas," Carcinogenesis, 2011, 32; 796-803.
Martin-Subero et al., "Towards defining the lymphoma methylome," Leukemia, Oct. 2006, 20(10):1658-1660.
Masutomi et al., "The telomerase reverse transcriptase regulates chromatin state and DNA damage responses," PNAS, Jun. 2005, 102(23):8222-8227.
Melero et al., "Il-12 gene therapy for cancer: in synergy with other immunotherapies," Trends Immunol., Mar. 2001, 22(3):113-115.
Meyne et al., "Distribution of non-telolneric sites of the (TT AGGG)n telomeric sequence in vertebrate chromosomes," Chromosoma, 1990, 99: 3-10.
Mineharu et al., "Blockade of mTOR signaling via rapamycin combined with immunotherapy augments antiglioma cytotoxic and memory T-cell functions," Mol. Cancer Ther., Dec. 2014, 13(12):3024-3036.
Minto et al., "Pharmacokinetics and pharmacodynamics of nandrolone esters in oil vehicle: effects of ester, injection site and injection volume," J. Pharmacol. Exp. Ther. 281(1):93-102.
Miranda et al., "Nucleic acids within urinary exosomes/microvesicles are potential biomarkers for renal disease," Kidney International, Jul. 2010, 78:191-199.
Moschella et al., "Combination strategies for enhancing the efficacy of immunotherapy in cancer patients." Ann NY Acad. Sci., 1194(1):169-178.
Neumann et al., "Plant centromeric retrotransposons: a structural and cytogenetic perspective," Mobile DNA, 2011, 2: 4.
Newton et al., "Anti-interleukin-10R1 monoclonal antibody in combination with bacillus Calmette—Guérin is protective against bladder cancer metastasis in a murine orthotopic tumour model and demonstrates systemic specific anti-tumour immunity," Clin. Exp. Immunol., Jul. 2014, 177(1):261-268.
Nordstrom et al., "Direct analysis of single-nucleotide polymorphism on double-stranded DNA by pyrosequencing." Biotechnol. Appl. Biochem., Apr. 2000, 31(2):107-112.
Office Action in European Application No. 15811533.7, dated Jan. 2, 2019, 4 pages.
Olivier et al., "TP53 mutations in human cancers: origins, consequences, and clinical use," Cold Spring Harb. Perspect. Biol., 2(1):a001008.
Ostro & Cullis., "Use of liposomes as injectable-drug delivery systems," Am. J. Hosp. Pharm. Aug. 1989, 46:1576-1587.
Ozsolak et al., "Amplification-free digital gene expression profiling from minute cell quantities," Nat Methods, Aug. 2010, 7: 619-621.
Park et al., "Telomerase modulates Wnt signalling by association with target gene chromatin," Nature, Jul. 2009, 460: 66-72.
PCT International Preliminary Report on Patentability in International Application No. PCT/US2015/037792, dated Dec. 27, 2016, 6 pages.
PCT International Preliminary Report on Patentability in International Application No. PCT/US2019/016898, dated Aug. 11, 2020, 11 pages.
PCT International Search Report and Written Opinion in International Appln. No. PCT/US2020/012085, dated Apr. 1, 2020, 10 pages.
PCT International Search Report and Written Opinion dated Apr. 26, 2019, in International Appln. No. PCT/US2019/16898, 14 pages.
PCT International Search Report and Written Opinion dated Oct. 28, 2015 in international application No. PCT/US2015/037792, 12 pages.

Pearce et al., "Enhancing CD8 T-cell memory by modulating fatty acid metabolism," Nature, Jul. 2009, 460(7251):103-107.
Pérez-Salvia and Esteller., "Bromodomain inhibitors and cancer therapy: From structures to applications," Epigenetics, May 2017, 12(5):323-339.
Peters et al., "Loss of the Suv39h Histone Methyltransferases Impairs Mammalian Heterochromatin and Genome Stability," Cell, Nov. 2001, 107: 323-337.
Petitjean et al., "Impact of mutant p53 functional properties on TP53 mutation patterns and tumor phenotype: lessons from recent developments in the IARC TP53 database," Hum. Mutat., Jun. 2007, 28(6):622-629.
Pfaffe et al., "Diagnostic potential of saliva: current state and future applications," Clin. Chem., May 2011, 57(5):675-687.
Philips et al., "Rapid point-of-care breath test for biomarkers of breast cancer and abnormal mammograms," PLOS One, Mar. 2014, 9(3):e90226.
Plohl et al., "Satellite DNAs between selfishness and functionality: Structure, genomics and evolution of tandem repeats in centromeric (hetero)chromatin," Gene, 2008, 409: 72-82.
Portielje et al., "IL-12: a promising adjuvant for cancer vaccination," Cancer Immunol. Immunother., 52(3):133-144.
Pradeu & Cooper., "The danger theory: 20 years later," Front Immunol., 2012, 3:287-287.
Prosser et al., "Sequence relationships of three human satellite DNAs," J Mol Biol., Jan. 1986, 187(2):145-55.
Rao., "Recent developments of collagen-based materials for medical applications and drug delivery systems," J. Biomater Sci. Polym. Ed., Dec. 1994, 7(7):623-645.
Richards et al., "The centromere region of *Arabidopsis thaliana* chromosome 1 contains telomere-similar sequences," Nucleic Acids Res, 1991, 19: 3351-3357.
Rizzi et al., "Transcriptional Activation of a Constitutive Heterochromatic Domain of the Human Genome in Response to Heat Shock," Mol Biol Cell, Feb. 2004, 15: 543-551.
Rohatagi et al., "Pharmacokinetic and pharmacodynamic evaluation of triamcinolone acetonide after intravenous, oral, and inhaled administration," J. Clin. Pharmacol., Nov. 1995 35(12):1187-1193.
Rooney et al., "Molecular and genetic properties of tumors associated with local immune cytolytic activity," Cell, Jan. 2015, 160(1-2):48-61.
Roulois et al., "DNA-Demethylating Agents Target Colorectal Cancer Cells by Inducing Viral Mimicry by Endogenous Transcripts," Cell, Aug. 2015, 162(5):961-973.
Ruffell & Coussens, "Macrophages and therapeutic resistance in cancer," Cancer Cell. Apr. 2015, 27(4): 462-472.
Sharma et al., "2A peptides provide distinct solutions to driving stop-carry on translational recoding," Nucleic Acids Res, Apr. 2012, 40: 3143-3151.
Sharma., "Corrections: Barrett's Esophagus," N. Engl. J. Med. Apr. 2010, 362(15):1450.
Shiao et al., "Immune microenvironments in solid tumors: new targets for therapy," Genes & Dev., Dec. 2011, 25: 2559-2572.
Simonet et al., "The human TTAGGG repeat factors 1 and 2 bind to a subset of interstitial telomeric sequences and satellite repeats," Cell Res, 2011, 21: 1028-1038.
Smet & Loriot., "DNA hypomethylation in cancer: epigenetic scars of a neoplastic journey," Epigenetics, Apr. 2010, 5(3):206-213.
Smith, "Evolution of repeated DNA sequences by unequal crossover," Science, Feb. 1976, 191: 528-535.
Snyder et al., "Contribution of systemic and somatic factors to clinical response and resistance to PD-L1 blockade in urothelial cancer: an exploratory multi-omic analysis," PLoS Med., 14(5):e1002309.
Solovyov et al., "Global cancer transcriptome quantifies repeat element polarization between immunotherapy responsive and T cell suppressive classes," Cell Reports, Apr. 2018, 23(2):512-521.
Stewart & Smyth., "Improving cancer immunotherapy by targeting tumor-induced immune suppression," Cancer Metastasis Rev., Mar. 2011, 30(1):125-140.
Stump et al., "The use of modified primers to eliminate cycle sequencing artifacts," Nucleic Acids Research, 1999, 27(23):4642-4648.

(56) References Cited

OTHER PUBLICATIONS

Tanne et al., "Distinguishing the immunostimulatory properties of noncoding RNAs expressed in cancer cells," Proc. Natl. Acad. Sci. USA., Dec. 2015, 112(49):15154-15159.
Tarhini & Iqbal., "CTLA-4 blockade: therapeutic potential in cancer treatments," Onco Targets Ther., Jun. 2010, 3: 15-25.
Taube et al., "Implications of the tumor immune microenvironment for staging and therapeutics," Mod. Pathol., Dec. 2017, 31(2):214-234.
Taylor & Gercel-Taylor., "The origin, function, and diagnostic potential of RNA within extracellular vesicles present in human biological fluids," Front. Genet. Jul. 2013, 4:142.
Tek and Jiang, "The centromeric regions of potato chromosomes contain megabase-sized tandem arrays of telomere-similar sequence," Chromosoma, Sep. 2004, 113: 77-83.
Topalian et al., "Safety, Activity, and Immune Correlates of Anti—PD-1 Antibody in Cancer," N. Engl. J. Med., Jun. 2012, 366(26):2443-2454.
Urbanek et al., "Small RNA Detection by in Situ Hybridization Methods," Int. J. Mol. Sci., Jun. 2015, 16(6):13259-13286.
Vilar & Gruber., "Microsatellite instability in colorectal cancer-the stable evidence," Nat. Rev. Clin. Oncol., Mar. 2010, 7(3):153-162.
Villasante et al., "Centromeres were derived from telomeres during the evolution of the eukaryotic chromosome," PNAS, Jun. 2007, 104: 10542-7.
Wang et al., "Cyclohexene nucleic acids (CeNA): serum stable oligonucleotides that activate RNase H and increase duplex stability with complementary RNA," J. Am. Chem. Soc., Sep. 2000, 122(36):8595-8602.
Warburton et al., "Analysis of the largest tandemly repeated DNA families in the human genome," BMC Genomics, 2008, 9:533.
Ward-Hartstonge & Kemp., "Regulatory T-cell heterogeneity and the cancer immune response," Clin. Transl. Immunology, Sep. 2017, 6(9):e154.
Watts et al., "Gene silencing by siRNAs and antisense oligonucleotides in the laboratory and the clinic," J. Pathol., Jan. 2012, 226(2):365-379.
Wojtowicz-Praga., "Reversal of tumor-induced immunosuppression by TGF-β inhibitors," Invest. New Drugs, Feb. 2003, 21(1): 21-32.
Wyczechowska et al., "The effects of cladribine and fludarabine on DNA methylation in K562 cells," Biochem Pharmacol., Jan. 2003, 65(2): 219-225.
Xi et al., "Copy number variation detection in whole-genome sequencing data using the Bayesian information criterion," PNAS, 2011, 108: E1128-E1136.
Yang et al., "Detection of tumor cell-specific mRNA and protein in exosome-like microvesicles from blood and saliva," PLoS One, Nov. 2014, 9(11):e110641.
Yasun et al., "Enrichment and detection of rare proteins with aptamer-conjugated gold nanorods," Anal. Chem., Jun. 2012, 84(14):6008-6015.
Yu et al., "Epigenetics and chronic lymphocytic leukemia," Am. J. Hematol., Nov. 2006, 81(11): 864-869.
Zahn et al., "Expansion of a novel endogenous retrovirus throughout the pericentromeres of modern humans," Genome Biol., Dec. 2015, 16(1):74, 24 pages.
Zeisberger et al., "Clodronate-liposome-mediated depletion of tumour-associated macrophages: a new and highly effective antiangiogenic therapy approach," Br. J. Cancer, Aug. 2006, 95(3): 272-281.
Zhdanova et al., "Unusual distribution pattern of telomeric repeats in the shrews Sorex araneus and Sorex granaries," Chromosome Res, Aug. 2005, 13: 617-625.
Zhu et al., "BRCA1 tumor suppression occurs via heterochromatin mediated silencing," Nature, 2011, 477: 179-184.
Zitvogel et al., "Mechanism of action of conventional and targeted anticancer therapies: reinstating immunosurveillance," Immunity, Jul. 2013, 39(1):74-88.

\* cited by examiner

BIOMARKERS OF CANCER

CLAIM OF PRIORITY

This application is a continuation application of U.S. Ser. No. 13/877,373, filed on Oct. 10, 2013, which is a § 371 National Stage Application of PCT/US2011/055108, filed on Oct. 6, 2011, which claims the benefit of U.S. Provisional Patent Application Ser. No. 61/390,956, filed on Oct. 7, 2010, and 61/493,800, filed on Jun. 6, 2011. The entire contents of the foregoing are hereby incorporated by reference.

TECHNICAL FIELD

This invention relates to methods of diagnosing cancer, based on detecting the presence of increased levels of expression of satellite repeats and/or Line-1.

BACKGROUND

Genome-wide sequencing approaches have revealed an increasing set of transcribed non-coding sequences, including "pervasive transcription" by heterochromatic regions of the genome linked to transcriptional silencing and chromosomal integrity (J. Berretta, A. Morillon, EMBO Rep 10, 973 (September, 2009); A. Jacquier, Nat Rev Genet 10, 833 (December, 2009)). In the mouse, heterochromatin is comprised of centric (minor) and pericentric (major) satellite repeats that are required for formation of the mitotic spindle complex and faithful chromosome segregation (M. Guenatri, D. Bailly, C. Maison, G Almouzni, J Cell Biol 166, 493 (Aug. 16, 2004)), whereas human satellite repeats have been divided into multiple classes with similar functions (J. Jurka et al., Cytogenet Genome Res 110, 462 (2005)). Bidirectional transcription of satellites in yeast maintains silencing of centromeric DNA through the Dicer mediated RNA-induced transcriptional silencing (RITS) and through a recently identified Dicer-independent pathway (M. Halic, D. Moazed, Cell 140, 504 (February 19)), although centromeric satellite silencing mechanisms in mammals are less well defined (A. A. Aravin, G J. Hannon, J. Brennecke, Science 318, 761 (Nov. 2, 2007)). Accumulation of satellite transcripts in mouse and human cell lines results from defects in DICER1 (C. Kanellopoulou et al., Genes Dev 19, 489 (Feb. 15, 2005); T. Fukagawa et al., Nat Cell Biol 6, 784 (August, 2004)) and from DNA demethylation, heat shock, or the induction of apoptosis (H. Bouzinba-Segard, A. Guais, C. Francastel, Proc Natl Acad Sci USA 103, 8709 (Jun. 6, 2006); R. Valgardsdottir et al., Nucleic Acids Res 36, 423 (February, 2008)). Stress-induced transcription of satellites in cultured cells has also been linked to the activation of retroelements encoding RNA polymerase activity such as LINE-1 (L1TD1)(D. Ugarkovic, EMBO Rep 6, 1035 (November, 2005); D. M. Carone et al., Chromosoma 118, 113 (February, 2009)). Despite these in vitro models, the global expression of repetitive ncRNAs in primary tumors has not been analyzed, due to the bias of microarray platforms toward annotated coding sequences and the specific exclusion of repeat sequences from standard analytic programs.

SUMMARY

The present invention is based, at least in part, on the identification of massive expression of satellite repeats in tumor cells, and of increased levels of Line-1, e.g., in tumor cells including circulating tumor cells (CTCs). Described herein are methods for diagnosing cancer, e.g., solid malignancies of epithelial origin such as pancreatic, lung, breast, prostate, renal, ovarian or colon cancer, based on the presence of increased levels of expression of satellite repeats and/or Line-1.

In a first aspect, the invention provides methods, e.g., in vitro methods, for detecting the presence of cancer in a subject, including determining a level of LINE-1 in a sample from the subject to obtain a test value; and comparing the test value to a reference value, wherein a test value compared to the reference value indicates whether the subject has cancer.

In some embodiments, the reference value represents a threshold level of LINE-1, wherein the presence of a level of LINE-1 in the subject that is above the reference value indicates that the subject has cancer, and the presence of a level of LINE-1 in the subject that is below the reference value indicates that the subject is unlikely to have cancer.

In a first aspect, the invention provides methods, e.g., in vitro methods, for detecting the presence of cancer in a subject, including determining a level of satellite transcripts in a sample from the subject to obtain a test value; and comparing the test value to a reference value, wherein a test value compared to the reference value indicates whether the subject has cancer.

In some embodiments, the satellite transcripts comprise one or more of ALR, HSATII, GSATII, TAR1, and SST1. In some embodiments, the satellite transcript is ALR and/or HSATII, and the presence of a level of ALR and/or HSATII satellite transcripts above the reference level indicates that the subject has a tumor.

In some embodiments, the satellite transcript is GSATII, TAR1 and/or SST1, and the presence of a level of GSATII, TAR1 and/or SST1 satellite transcripts below the reference level indicates that subject has a tumor.

In another aspect, the invention provides methods, e.g., in vitro methods, for evaluating the efficacy of a treatment for cancer in a subject. The methods include determining a level of LINE-1 in a first sample from the subject to obtain a first value; administering a treatment for cancer to the subject; determining a level of LINE-1 in a subsequent sample obtained from the subject at a later time, to obtain a treatment value; and comparing the first value to the treatment value. A treatment value that is below the first value indicates that the treatment is effective.

In yet another aspect, the invention provides methods, e.g., in vitro methods, for evaluating the efficacy of a treatment for cancer in a subject. The methods include determining a level of satellite transcripts in a first sample from the subject to obtain a first value; administering a treatment for cancer to the subject; determining a level of satellite transcripts in a subsequent sample obtained from the subject at a later time, to obtain a treatment value; and comparing the first value to the treatment value, wherein a treatment value that is below the first value indicates that the treatment is effective.

In some embodiments, the satellite transcripts comprise one or more of ALR, HSATII, GSATII, TAR1, and SST1.

In some embodiments, the first and second samples are known or suspected to comprise tumor cells, e.g., blood samples known or suspected of comprising circulating tumor cells (CTCs), or biopsy samples known or suspected of comprising tumor cells. In some embodiments, the sample comprises free RNA in serum or RNA within exosomes in blood.

In some embodiments, the treatment includes administration of a surgical intervention, chemotherapy, radiation therapy, or a combination thereof.

In some embodiments of the methods described herein, the subject is a mammal, e.g., a human or veterinary subject, e.g., experimental animal.

In some embodiments of the methods described herein, the cancer is a solid tumor of epithelial origin, e.g., pancreatic, lung, breast, prostate, renal, ovarian or colon cancer.

In some embodiments, the methods described herein include measuring a level of LINE-1 transcript.

In some embodiments of the methods described herein, the level of a LINE-1 transcript or satellite is determined using a branched DNA assay.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
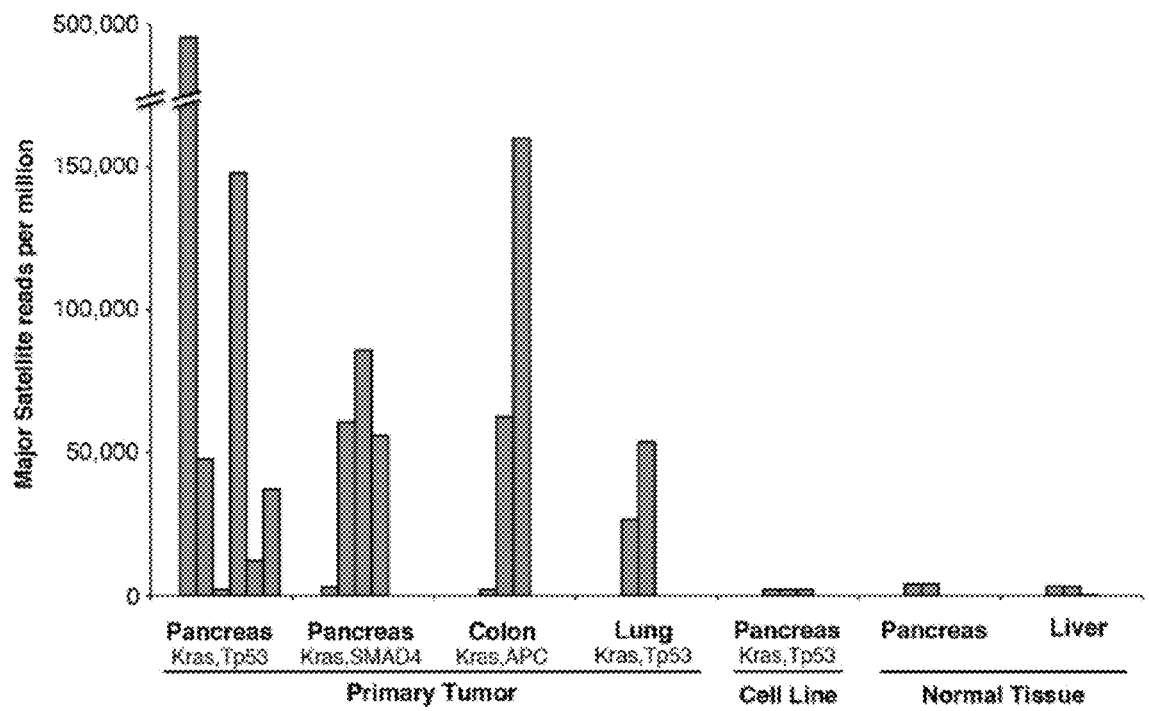
FIG. 1A is a bar graph showing levels of major satellite in percent of all genomic aligned reads among different tumors, cell lines, and tissues. Genotype of primary tumors and cell lines indicated below each tumor type and cell line. (Kras=KrasG12D; Tp53, SMAD4, and APC represent genes deleted)

The present invention is based, at least in part, on the identification of a massive generation of LINE-1 protein and bidirectional ncRNAs from the major satellite repeat in mouse tumor models and from ALR and HSATII satellite repeats in human cancers. The exceptional magnitude of satellite levels in these cancers is unprecedented. This is likely to result from a general derepression of chromosomal marks affecting both satellites and LINE-1 retrotransposons, with proximity to LINE-1 activation potentially affecting the expression of selected cellular mRNAs. Together, the very high expression of satellites may affect chromosomal integrity and genetic stability, while the co-deregulated coding sequences may affect cell fates and biological behavior of cancer cells. In addition, the finding of massive expression of specific satellite subsets in human pancreatic cancer provides a novel biomarker for application in early detection of cancer. Finally, levels of LINE-1 are increased in circulating tumor cells from subjects with newly diagnosed metastatic pancreatic adenocarcinoma. Thus the present methods are useful in the early detection of cancer, and can be used to predict clinical outcomes.

Diagnosing Cancer Using Transcript Biomarkers

The methods described herein can be used to diagnose the presence of, and monitor the efficacy of a treatment for, cancer, e.g., solid tumors of epithelial origin, e.g., pancreatic, lung, breast, prostate, renal, ovarian or colon cancer, in a subject.

As used herein, the term "hyperproliferative" refer to cells having the capacity for autonomous growth, i.e., an abnormal state or condition characterized by rapidly proliferating cell growth. Hyperproliferative disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A "tumor" is an abnormal growth of hyperproliferative cells. "Cancer" refers to pathologic disease states, e.g., characterized by malignant tumor growth.

As demonstrated herein, the presence of cancer, e.g., solid tumors of epithelial origin, e.g., as defined by the ICD-O (International Classification of Diseases-Oncology) code (revision 3), section (8010-8790), e.g., early stage cancer, is associated with the presence of a massive levels of satellite due to increase in transcription and processing of satellite repeats in pancreatic cancer cells, and of increased levels of LINE-1 expression in circulating tumor cells. Thus the methods can include the detection of expression levels of satellite repeats in a sample comprising cells known or suspected of being tumor cells, e.g., cells from solid tumors of epithelial origin, e.g., pancreatic, lung, breast, prostate, renal, ovarian or colon cancer cells. Alternatively or in addition, the methods can include the detection of increased levels of LINE-1 in a sample, e.g., a sample known or suspected of including tumor cells, e.g., circulating tumor cells (CTCs), e.g., using a microfluidic device as described herein.

Cancers of epithelial origin can include pancreatic cancer (e.g., pancreatic adenocarcinoma or intraductal papillary mucinous carcinoma (IPMN, pancreatic mass)), lung cancer (e.g., non-small cell lung cancer), prostate cancer, breast cancer, renal cancer, ovarian cancer, or colon cancer. For example, the present methods can be used to distinguish between benign IPMN, for which surveillance is the standard treatment, and malignant IPMN, which require resection, a procedure associated with significant morbidity and a small but significant possibility of death. In some embodiments, in a subject diagnosed with IPMN, the methods described herein can be used for surveillance/monitoring of the subject, e.g., the methods can be repeated at selected intervals (e.g., every 3, 6, 12, or 24 months) to determine whether a benign IPMN has become a malignant IPMN warranting surgical intervention. In addition, in some embodiments the methods can be used to distinguish bronchioloalveolar carcinomas from reactive processes (e.g., postpneumonic reactive processes) in samples from subjects suspected of having non-small cell lung cancer. In some embodiments, in a sample from a subject who is suspected of having breast cancer, the methods can be used to distinguish ductal hyperplasia from atypical ductal hyperplasia and ductal carcinoma in situ (DCIS). The two latter categories receive resection/radiation; the former does not require intervention. In some embodiments, in subjects suspected of having prostate cancer, the methods can be used to distinguish between atypical small acinar proliferation and malignant cancer. In some embodiments, in subjects suspected of having bladder cancer, the methods can be used to detect, e.g., transitional cell carcinoma (TCC), e.g., in urine specimens. In some embodiments, in subjects diagnosed with Barrett's Esophagus (Sharma, N Engl J Med. 2009, 24; 361(26):2548-56. Erratum in: N Engl J Med. 2010 April 15; 362(15):1450), the methods can be used for distinguishing dysplasia in Barrett's esophagus from a reactive process. The clinical implications are significant, as a diagnosis of dysplasia demands a therapeutic intervention. Other embodiments include, but are not limited to, diagnosis of well differentiated hepatocellular carcinoma, ampullary and bile duct carcinoma, glioma vs. reactive gliosis, melanoma vs. dermal nevus, low grade sarcoma, and pancreatic endocrine tumors, inter alia.

Therefore, included herein are methods for diagnosing cancer, e.g., tumors of epithelial origin, e.g., pancreatic, lung, breast, prostate, renal, ovarian or colon cancer, in a subject. In some embodiments, the methods include obtaining a sample from a subject, and evaluating the presence and/or level of LINE-1 or satellites in the sample, and comparing the presence and/or level with one or more references, e.g., a control reference that represents a normal level of LINE-1 or satellites, e.g., a level in an unaffected subject or a normal cell from the same subject, and/or a disease reference that represents a level of LINE-1 or satellites associated with cancer, e.g., a level in a subject having pancreatic, lung, breast, prostate, renal, ovarian or colon cancer.

The present methods can also be used to determine the stage of a cancer, e.g., whether a sample includes cells that are from a precancerous lesion, an early stage tumor, or an advanced tumor. For example, the present methods can be used to determine whether a subject has a precancerous pancreatic, breast, or prostate lesion. Where the markers used are LINE-1, or satellite transcript ALR and/or HSATII, increasing levels are correlated with advancing stage. For satellite transcripts GSATII, TAR1 and/or SST1, decreasing levels are correlated with increasing stage. Additionally, levels of LINE-1 and satellite ALR and/or HSATII may be prognostic and predictive to clinical outcomes.

Samples

In some embodiments of the present methods, the sample is or includes blood, serum, and/or plasma, or a portion or subfraction thereof, e.g., free RNA in serum or RNA within exosomes in blood. In some embodiments, the sample comprises (or is suspected of comprising) CTCs. In some embodiments, the sample is or includes urine or a portion or subfraction thereof. In some embodiments, the sample includes known or suspected tumor cells, e.g., is a biopsy sample, e.g., a fine needle aspirate (FNA), endoscopic biopsy, or core needle biopsy; in some embodiments the sample comprises cells from the pancreatic, lung, breast, prostate, renal, ovarian or colon of the subject. In some embodiments, the sample comprises lung cells obtained from a sputum sample or from the lung of the subject by brushing, washing, bronchoscopic biopsy, transbronchial biopsy, or FNA, e.g., bronchoscopic, fluoroscopic, or CT-guided FNA (such methods can also be used to obtain samples from other tissues as well). In some embodiments, the sample is frozen, fixed and/or permeabilized, e.g., is an formalin-fixed paraffin-embedded (FFPE) sample.

Satellite Expression Levels

In some embodiments, the level of satellite transcripts is detected, e.g., in a sample known or suspected to include tumor cells. In some embodiments, the level of satellite transcripts in a known or suspected tumor cell, e.g., a test cell, is compared to a reference level.

In some embodiments, the methods include detecting levels of alpha (ALR) satellite transcripts (D. Lipson et al., Nat Biotechnol 27, 652 (July, 2009)) or HSATII satellite transcripts (J. Jurka et al., Cytogenet Genome Res 110, 462 (2005)); in some embodiments, those levels are compared to a reference. In some embodiments, the reference level is a level of ALR and/or HSATII satellite transcripts in a normal (non-cancerous) cell, e.g., a normal cell from the same subject, or a reference level determined from a cohort of normal cells; the presence of levels of ALR and/or HSATII in the test cell above those in the normal cell indicate that the test cell is a tumor cell (e.g., the subject from whom the test cell came has or can be diagnosed with cancer). In some embodiments, the reference level of ALR and/or HSATII transcripts is a threshold level, and the presence of a level of ALR and/or HSATII satellite transcripts above the threshold level indicates that the cell is a tumor cell (e.g., the subject from whom the test cell came has or can be diagnosed with cancer).

In some embodiments, the methods include detecting levels of GSATII, TAR1 and/or SST1 transcripts; in some embodiments, those levels are compared to a reference. In some embodiments, the reference level is a level of GSATII, TAR1 and/or SST1 satellite transcripts in a normal (non-cancerous) cell, e.g., a normal cell from the same subject, or a reference level determined from a cohort of normal cells; the presence of levels of GSATII, TAR1 and/or SST1 in the test cell below those in the normal cell indicate that the test cell is a tumor cell (e.g., the subject from whom the test cell came has or can be diagnosed with cancer). In some embodiments, the reference level of GSATII, TAR1 and/or SST1 transcripts is a threshold level, and the presence of a level of GSATII, TAR1 and/or SST1 satellite transcripts below the threshold level indicates that the cell is a tumor cell (e.g., the subject from whom the test cell came has or can be diagnosed with cancer).

In some embodiments, the levels of the satellite transcripts are normalized to a relatively non-variant transcript such as GAPDH, actin, or tubulin, e.g., the level of expression of the satellite is compared to the non-variant transcript. For example, a ratio of expression levels can be calculated, and the ratio can be compared to the ratio in a normal (non-cancerous) cell. For example, in some embodiments the presence of a ratio of ALR:GAPDH of over 10:1, e.g., over 50:1, over 100:1, or over 150:1, indicates that the test cell is a cancer cell; in some embodiments the presence of a ratio of ALR:GAPDH of about 3:1 or 5:1 indicates that the test cell is a normal cell. In some embodiments, the presence of a ratio of HSATII satellites:GAPDH transcripts of over 10:1, e.g., 20:1, 30:1, 40:1, or 45:1, indicates that the test cell is a cancer cell. In some embodiments, the presence of significant (e.g., more than about 100 transcripts per million aligned) levels of HSATII indicates that the test cell is a cancer cell. In some embodiments, the absence or presence of very low levels (e.g., less than about 20 transcripts per million aligned) of HSATII indicates that the test cell is a normal cell.

Below are exemplary reference sequences that can be used for ALR (including its variants) and HSATII transcripts:

```
>ALR SAT Homo sapiens
                                        (SEQ ID NO: 1)
aattctcagtaacttccttgtgttgtgtgtattcaactcacagagttgaa cgatcctttacacagagcagacttgaaacactcttttgtggaatttgca agtggagatttcagccgctttgaggtcaatggtagaataggaaatatctt cctatagaaactagacagaat >ALR1 SAT Homo sapiens
                                        (SEQ ID NO: 2)
tcattctcagaaactrctttgtgatgtgtgcrttcaactcacagagttta acctttcttttgatagagcagtttggaaacactctgtttgtaaagtctgc aagtggatatttggacctctttgaggccttcgttggaaacgggatttctt catataatgctagacagaaga >ALR2 SAT Homo sapiens
                                        (SEQ ID NO: 3)
agctttctgagaaactgctttgtgatgtgtgcattcatctcacagagtta aacctttcttttgattcagcagtttggaaacactgttttttgtagaatctg tgaagggatatttgggagctcattgaggcctatggtgaaaaagaaaatat cttcagataaaaactagaaggaagctatc >ALRa SAT Primates
                                        (SEQ ID NO: 4)
ctatctgagaaactgctttgtgatgtgtgcattcatctcacagagttaaa cctttcttttgattcagcagtttggaaacactgtttttgtagaatctgcg aagggacatttgggagctcattgaggcctatggtgaaaaagcgaatatcc ccagataaaaactagaaagaag >ALRa_ SAT Primates
                                        (SEQ ID NO: 5)
ttgtagaatctgcgaagggacatttgggagctcattgaggcctatggtga aaaagcgaatatcccccagataaaaactagaaagaagctatctgagaaact gctttgtgatgtgtgcattcatctcacagagttaaacctttcttttgatt cagcagtttggaaacactgttt >ALRb SAT Primates
                                        (SEQ ID NO: 6)
ttgtggaatttgcaagtggagatttcaagcgctttgaggccaawnktaga aaaggaaatatcttcgtataaaaactagacagaataattctcagtaactt ctttgtgttgtgtgtattcaactcacagagttgaaccttccttttagacag agcagatttgaaacactcttt
```

-continued

>ALR_ SAT Primates (SEQ ID NO: 7)

ttgtagaatctgcaagtggatatttggasckctttgaggmcttcgktgga aacgggaatatcttcacataaaaactagacagaagcattctcagaaactt ctttgtgatgtttgcattcaactcacagagttgaacmttccttttgatag agcagttttgaaacactcttt >HSATII SAT Primates (SEQ ID NO: 8)

ccattcgattccattcgatgattccattcgattccattcgatgatgattc cattcgattccattcgatgattccattcgattccattcgatgatgattcc attcgattccattcgatgattccattcgattccattcgatgatgattcca ttcgattccattcgatgatt Line-1 Levels Long interspersed nucleotide element (LINE) non-LTR retrotransposons (Singer, Cell 28 (3): 433-4 (1982)) are a group of genetic elements that are found in large numbers in eukaryotic genomes, and generate insertion mutations, contribute to genomic instability and innovation, and can alter gene expression.

The canonical, full-length LINE-1 element is about 6 kilobases (kb) in length and includes a 5' untranslated region (UTR) with an internal RNA polymerase II promoter (Swergold, Mol Cell Biol. 10(12):6718-29 (1990)), two open reading frames (designated ORF1 and ORF2) and a 3' UTR containing a polyadenylation signal ending with an oligo dA-rich tail of variable length (Babushok and Kazazian, Hum Mutat. 28(6):527-39 (2007)). Although there are over 500,000 L1 elements inserted in the human genome, only about 80-100 copies are retrotransposition-competent (Brouha et al., Proc Natl Acad Sci USA. 100(9):5280-5. (2003)). For additional details, see Cordaux and Batzer, Nat Rev Genet. 10(10): 691-703 (2009)).

Exemplary LINE-1 sequences include GenBank Ref. No. NM_001164835.1 (nucleic acid) and NP_001158307.1 (protein) for variant (1); and GenBank Ref. No. NM_019079.4 (nucleic acid) and NP_061952.3 (protein) for variant 2, which is the shorter transcript. Variant 2 differs in the 5' UTR compared to variant 1, but both variants 1 and 2 encode the same protein. See also Gene ID: 54596.

In some embodiments, the methods for diagnosing cancer described herein include determining a level of LINE-1 mRNA in a cell, e.g., in CTCs present in blood of a subject to obtain a LINE-1 value, and comparing the value to an appropriate reference value, e.g., a value that represents a threshold level, above which the subject can be diagnosed with cancer. The reference can also be a range of values, e.g., that indicate severity or stage of the cancer in the subject. A suitable reference value can be determined by methods known in the art.

In some embodiments, the reference level is a level of LINE-1 transcripts in a normal (non-cancerous) cell, e.g., a normal cell from the same subject, or a reference level determined from a cohort of normal cells; the presence of levels of LINE-1 in the test cell above those in the normal cell indicate that the test cell is a tumor cell (e.g., the subject from whom the test cell came has or can be diagnosed with cancer). In some embodiments, the reference level of LINE-1 transcripts is a threshold level, and the presence of a level of LINE-1 transcripts above the threshold level indicates that the cell is a tumor cell (e.g., the subject from whom the test cell came has or can be diagnosed with cancer).

Methods of Detection

Any methods known in the art can be used to detect and/or quantify levels of a biomarker as described herein. For example, the level of a satellite transcript or LINE-1 mRNA (transcript) can be evaluated using methods known in the art, e.g., Northern blot, RNA in situ hybridization (RNA-ISH), RNA expression assays, e.g., microarray analysis, RT-PCR, deep sequencing, cloning, Northern blot, and quantitative real time polymerase chain reaction (qRT-PCR). Analytical techniques to determine RNA expression are known. See, e.g., Sambrook et al., *Molecular Cloning: A Laboratory Manual*, 3rd Ed., Cold Spring Harbor Press, Cold Spring Harbor, N.Y. (2001).

In some embodiments, the level of the LINE-1 protein is detected. The presence and/or level of a protein can be evaluated using methods known in the art, e.g., using quantitative immunoassay methods such as enzyme linked immunosorbent assays (ELISAs), immunoprecipitations, immunofluorescence, immunohistochemistry, enzyme immunoassay (EIA), radioimmunoassay (RIA), and Western blot analysis.

In some embodiments, the methods include contacting an agent that selectively binds to a biomarker, e.g., to a satellite transcript or LINE-1 mRNA or protein (such as an oligonucleotide probe, an antibody or antigen-binding portion thereof) with a sample, to evaluate the level of the biomarker in the sample. In some embodiments, the agent bears a detectable label. The term "labeled," with regard to an agent encompasses direct labeling of the agent by coupling (i.e., physically linking) a detectable substance to the agent, as well as indirect labeling of the agent by reactivity with a detectable substance. Examples of detectable substances are known in the art and include chemiluminescent, fluorescent, radioactive, or colorimetric labels. For example, detectable substances can include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, quantum dots, or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$. In general, where a protein is to be detected, antibodies can be used. Antibodies can be polyclonal, or more preferably, monoclonal. An intact antibody, or an antigen-binding fragment thereof (e.g., Fab or $F(ab')_2$) can be used.

In some embodiments, high throughput methods, e.g., protein or gene chips as are known in the art (see, e.g., Ch. 12, "Genomics," in Griffiths et al., Eds. *Modern genetic Analysis*, 1999, W. H. Freeman and Company; Ekins and Chu, Trends in Biotechnology, 1999; 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of satellites or LINE-1.

In some embodiments, the methods include using a modified RNA in situ hybridization technique using a branched-chain DNA assay to directly detect and evaluate the level of biomarker mRNA in the sample (see, e.g., Luo et al., U.S.

Pat. No. 7,803,541B2, 2010; Canales et al., Nature Biotechnology 24(9):1115-1122 (2006); Nguyen et al., Single Molecule in situ Detection and Direct Quantification of miRNA in Cells and FFPE Tissues, poster available at panomics.com/index.php?id=product_87). A kit for performing this assay is commercially-available from Affymetrix (ViewRNA).

Detection of LINE-1 and Satellite Transcripts in CTCs

In some embodiments, microfluidic (e.g., "lab-on-a-chip") devices can be used in the present methods. Such devices have been successfully used for microfluidic flow cytometry, continuous size-based separation, and chromatographic separation. In general, methods in which expression of satellites or LINE-1 is detected in circulating tumor cells (CTCs) can be used for the early detection of cancer, e.g., early detection of tumors of epithelial origin, e.g., pancreatic, lung, breast, prostate, renal, ovarian or colon cancer.

The devices can be used for separating CTCs from a mixture of cells, or preparing an enriched population of CTCs. In particular, such devices can be used for the isolation of CTCs from complex mixtures such as whole blood.

A variety of approaches can be used to separate CTCs from a heterogeneous sample. For example, a device can include an array of multiple posts arranged in a hexagonal packing pattern in a microfluidic channel upstream of a block barrier. The posts and the block barrier can be functionalized with different binding moieties. For example, the posts can be functionalized with anti-EPCAM antibody to capture circulating tumor cells (CTCs); see, e.g., Nagrath et al., Nature 450:1235-1239 (2007), optionally with downstream block barriers functionalized with to capture LINE-1 nucleic acids or proteins, or satellites. See, e.g., (S. Maheswaran et al., N Engl J Med. 359, 366 (Jul. 24, 2008); S. Nagrath et al., Nature. 450, 1235 (Dec. 20, 2007); S. L. Stott et al., Sci Transl Med 2, 25ra23 (March 31)) and the applications and references listed herein.

Processes for enriching specific particles from a sample are generally based on sequential processing steps, each of which reduces the number of undesired cells/particles in the mixture, but one processing step may suffice in some embodiments. Devices for carrying out various processing steps can be separate or integrated into one microfluidic system. The devices include devices for cell/particle binding, devices for cell lysis, devices for arraying cells, and devices for particle separation, e.g., based on size, shape, and/or deformability or other criteria. In certain embodiments, processing steps are used to reduce the number of cells prior to introducing them into the device or system. In some embodiments, the devices retain at least 75%, e.g., 80%, 90%, 95%, 98%, or 99% of the desired cells compared to the initial sample mixture, while enriching the population of desired cells by a factor of at least 100, e.g., by 1000, 10,000, 100,000, or even 1,000,000 relative to one or more non-desired cell types.

Some devices for the separation of particles rely on size-based separation with or without simultaneous cell binding. Some size-based separation devices include one or more arrays of obstacles that cause lateral displacement of CTCs and other components of fluids, thereby offering mechanisms of enriching or otherwise processing such components. The array(s) of obstacles for separating particles according to size typically define a network of gaps, wherein a fluid passing through a gap is divided unequally into subsequent gaps. Both sieve and array sized-based separation devices can incorporate selectively permeable obstacles as described above with respect to cell-binding devices.

Devices including an array of obstacles that form a network of gaps can include, for example, a staggered two-dimensional array of obstacles, e.g., such that each successive row is offset by less than half of the period of the previous row. The obstacles can also be arranged in different patterns. Examples of possible obstacle shapes and patterns are discussed in more detail in WO 2004/029221.

In some embodiments, the device can provide separation and/or enrichment of CTCs using array-based size separation methods, e.g., as described in U.S. Pat. Pub. No. 2007/0026413. In general, the devices include one or more arrays of selectively permeable obstacles that cause lateral displacement of large particles such as CTCs and other components suspended in fluid samples, thereby offering mechanisms of enriching or otherwise processing such components, while also offering the possibility of selectively binding other, smaller particles that can penetrate into the voids in the dense matrices of nanotubes that make up the obstacles. Devices that employ such selectively permeable obstacles for size, shape, or deformability based enrichment of particles, including filters, sieves, and enrichment or separation devices, are described in International Publication Nos. 2004/029221 and 2004/113877, Huang et al. Science 304:987-990 (2004), U.S. Publication No. 2004/0144651, U.S. Pat. Nos. 5,837,115 and 6,692,952, and U.S. Application Nos. 60/703,833, 60/704,067, and Ser. No. 11/227,904; devices useful for affinity capture, e.g., those described in International Publication No. 2004/029221 and U.S. application Ser. No. 11/071,679; devices useful for preferential lysis of cells in a sample, e.g., those described in International Publication No. 2004/029221, U.S. Pat. No. 5,641,628, and U.S. Application No. 60/668,415; devices useful for arraying cells, e.g., those described in International Publication No. 2004/029221, U.S. Pat. No. 6,692,952, and U.S. application Ser. Nos. 10/778,831 and 11/146,581; and devices useful for fluid delivery, e.g., those described in U.S. application Ser. Nos. 11/071,270 and 11/227,469. Two or more devices can be combined in series, e.g., as described in International Publication No. WO 2004/029221. All of the foregoing are incorporated by reference herein.

In some embodiments, a device can contain obstacles that include binding moieties, e.g., monoclonal anti-EpCAM antibodies or fragments thereof, that selectively bind to particular cell types, e.g., cells of epithelial origin, e.g., tumor cells. All of the obstacles of the device can include these binding moieties; alternatively, only a subset of the obstacles include them. Devices can also include additional modules, e.g., a cell counting module or a detection module, which are in fluid communication with the microfluidic channel device. For example, the detection module can be configured to visualize an output sample of the device.

In one example, a detection module can be in fluid communication with a separation or enrichment device. The detection module can operate using any method of detection disclosed herein, or other methods known in the art. For example, the detection module includes a microscope, a cell counter, a magnet, a biocavity laser (see, e.g., Gourley et al., J. Phys. D: Appl. Phys., 36: R228-R239 (2003)), a mass spectrometer, a PCR device, an RT-PCR device, a microarray, RNA in situ hybridization system, or a hyperspectral imaging system (see, e.g., Vo-Dinh et al., IEEE Eng. Med. Biol. Mag., 23:40-49 (2004)). In some embodiments, a computer terminal can be connected to the detection module. For instance, the detection module can detect a label that selectively binds to cells, proteins, or nucleic acids of interest, e.g., LINE-1 DNA, mRNA, or proteins, or satellite DNA or mRNA.

In some embodiments, the microfluidic system includes (i) a device for separation or enrichment of CTCs; (ii) a device for lysis of the enriched CTCs; and (iii) a device for detection of LINE-1 DNA, mRNA, or proteins, or satellite DNA or mRNA.

In some embodiments, a population of CTCs prepared using a microfluidic device as described herein is used for analysis of expression of LINE-1 and/or satellites using known molecular biological techniques, e.g., as described above and in Sambrook, *Molecular Cloning: A Laboratory Manual*, Third Edition (Cold Spring Harbor Laboratory Press; 3rd edition (Jan. 15, 2001)); and *Short Protocols in Molecular Biology*, Ausubel et al., eds. (Current Protocols; 52 edition (Nov. 5, 2002)).

In general, devices for detection and/or quantification of expression of satellites or LINE-1 in an enriched population of CTCs are described herein and can be used for the early detection of cancer, e.g., tumors of epithelial origin, e.g., early detection of pancreatic, lung, breast, prostate, renal, ovarian or colon cancer.

Methods of Monitoring Disease Progress or Treatment Efficacy

In some embodiments, once it has been determined that a person has cancer, or has an increased risk of developing cancer, then a treatment, e.g., as known in the art, can be administered. The efficacy of the treatment can be monitored using the methods described herein; an additional sample can be evaluated after (or during) treatment, e.g., after one or more doses of the treatment are administered, and a decrease in the level of LINE-1, and/or ALR and/or HSATII satellites expression, or in the number of LINE-1-, and/or ALR and/or HSATII satellite-expressing cells in a sample, would indicate that the treatment was effective, while no change or an increase in the level of LINE-1, and/or ALR and/or HSATII satellite expression or LINE-1-, and/or ALR and/or HSATII satellite-expressing cells would indicate that the treatment was not effective (the converse would of course be true for levels of GSATII, TAR1 and/or SST1 satellites). The methods can be repeated multiple times during the course of treatment, and/or after the treatment has been concluded, e.g., to monitor potential recurrence of disease.

In some embodiments, e.g., for subjects who have been diagnosed with a benign condition that could lead to cancer, subjects who have been successfully treated for a cancer, or subjects who have an increased risk of cancer, e.g., due to a genetic predisposition or environmental exposure to cancer-causing agents, the methods can be repeated at selected intervals, e.g., at 3, 6, 12, or 24 month intervals, to monitor the disease in the subject for early detection of progression to malignancy or development of cancer in the subject.

EXAMPLES

The invention is further described in the following examples, which do not limit the scope of the invention described in the claims.

Example 1. Major Satellite Levels are Massively Elevated in Tumor Tissues Compared to Cell Lines and Normal Tissue The next generation digital gene expression (DGE) application from Helicos BioSciences (D. Lipson et al., Nat Biotechnol 27, 652 (July, 2009)) was utilized to compare expression of tumor markers in primary cancers and their derived metastatic precursors. We first determined DGE profiles of primary mouse pancreatic ductal adenocarcinoma (PDAC) generated through tissue-targeted expression of activated Kras and loss of Tp53 ($Kras^{G12D}$, $Tp53^{lox/+}$) (N. Bardeesy et al., Proc Natl Acad Sci USA 103, 5947 (Apr. 11, 2006)). These tumors are histopathological and genetic mimics of human PDAC, which exhibits virtually universal mutant KRAS (>90% of cases) and loss of TP53 (50-60%).

Mice with pancreatic cancer of different genotypes were bred as previously described in the Bardeesy laboratory (Bardeesy et al., Proc Natl Acad Sci USA 103, 5947 (2006)). Normal wild type mice were purchased from Jackson laboratories. Animals were euthanized as per animal protocol guidelines. Pancreatic tumors and normal tissue were extracted sterilely and then flash frozen with liquid nitrogen. Tissues were stored at −80° C. Cell lines were generated fresh for animals AH367 and AH368 as previously described (Aguirre et al., Genes Dev 17, 3112 (2003)) and established cell lines were cultured in RPMI-1640+10% FBS+1% Pen/Strep (Gibco/Invitrogen). Additional mouse tumors from colon and lung were generously provided by Kevin Haigis (Massachusetts General Hospital) and Kwok-Kin Wong (Dana Farber Cancer Institute).

Fresh frozen tissue was pulverized with a sterile pestle in a microfuge tube on dry ice. Cell lines were cultured and fresh frozen in liquid nitrogen prior to nucleic acid extraction. RNA and DNA from cell lines and fresh frozen tumor and normal tissues were all processed in the same manner. RNA was extracted using the TRIzol® Reagent (Invitrogen) per manufacturer's specifications. DNA from tissue and cell lines was extracted using the QIAamp Mini Kit (QIAGEN) per manufacturer's protocol.

Purified RNA was subjected to Digital Gene Expression (DGE) sample prepping and analysis on the HeliScope™ Single Molecule Sequencer from Helicos BioSciences. This method has been previously described (Lipson et al., Nat Biotechnol 27, 652 (2009)). Briefly, Single stranded cDNA was reverse transcribed from RNA with a dTU25V primer and the Superscript III cDNA synthesis kit (Invitrogen). RNA was digested and single stranded cDNA was purified using a solid phase reversible immobilization (SPRI) technique with Agencourt® AMPure® magnetic beads. Single stranded cDNA was denatured and then a poly-A tail was added to the 3' end using terminal transferase (New England Biolabs).

Purified DNA was subjected to the DNA sequencing sample prepping protocol from Helicos that has been previously described (Pushkarev, N. F. Neff, S. R. Quake, Nat Biotech 27, 847 (2009)). Briefly, genomic DNA was sheared with a Covaris S2 acoustic sonicator producing fragments averaging 200 bps and ranging from 100-500 bps. Sheared DNA was then cleaned with SPRI. DNA was then denatured and a poly-A tail was added to the 3' end using terminal transferase.

Tailed cDNA or DNA were then hybridized to the sequencing flow cell followed by "Fill and Lock" and single molecule sequencing. Gene expression sequence reads were then aligned to the known human or mouse transcriptome libraries using the DGE program. Genomic DNA sequence reads were aligned to the mouse genome and counted to determine copy number of the major mouse satellite (CNV).

The first mouse pancreatic tumor analyzed, AH284, was remarkable in that DGE sequences displayed a 48-52% discrepancy with the annotated mouse transcriptome, compared with a 3-4% difference for normal liver transcripts from the same mouse. Nearly all the discrepant sequences mapped to the pericentric (major) mouse satellite repeat. The satellite transcript accounts for ~49% (495,421 tpm) of all cellular transcripts in the tumor, compared with 0.02-0.4% (196-4,115 tpm) in normal pancreas or liver (Table 1).

TABLE 1

Total genomic aligned reads with breakdown of major satellite and transcriptome reads. Percentage of total genomic aligned reads in parentheses

|  | Total Reads | Major Satellite Reads | Transcriptome |
|---|---|---|---|
| Pancreatic Tumor | 18,063,363 | 8,460,135 (47%) | 1,726,768 (10%) |
| Normal Liver | 2,270,669 | 8,973 (0.4%) | 1,718,489 (75%) |
| Normal Pancreas | 492,301 | 2,026 (0.4%) | 63,160 (13%) |

Satellite sequence reads were found in both sense and anti-sense directions and are absent from poly-A purified RNA. Tumor AH284 therefore contained massive amounts of a non-polyadenylated dsRNA element, quantitatively determined as >100-fold increased over that present in normal tissue from the same animal. By way of comparison, the levels of satellite transcripts in tumor tissues were about 8,000-fold higher than the abundant mRNA Gapdh. A second independent pancreatic tumor nodule from the same mouse showed a lower, albeit still greatly elevated, level of satellite transcript (4.5% of total cellular transcripts).

Analysis of 4 additional pancreatic tumors from ($Kras^{G12D}$, $Tp53^{lox/+}$) mice and 4 mice with an alternative pancreatic tumorigenic genotype ($Kras^{G12D}$, $SMAD4^{lox/lox}$) revealed increased satellite expression in 6/8 additional tumors (range 1-15% of all cellular transcripts). In 2/3 mouse colon cancer tumors ($Kras^{G12D}$, $APC^{lox/+}$) and 2/2 lung cancers ($Kras^{G12D}$, $Tp53^{lox/lox}$), satellite expression level ranged from 2-16% of all cellular transcripts. In total, 12/15 (80%) independent mouse tumors had greatly increased levels of satellite expression, compared to normal mouse tissues (FIG. 1A, Table 2).

TABLE 2

Total genomic reads and percentage of reads aligning to transcriptome and major satellite among multiple mouse tumors, cell lines, and normal tissues.

| Mouse ID | Tissue Type | Genotype | Total Genomic Reads | % Transcriptome Reads | % Major Satellite Reads |
|---|---|---|---|---|---|
| AH284 Rep 1 | Pancreatic Cancer | $Kras^{G12D}$, $Tp53^{lox/+}$ | 18,063,363 | 9.56% | 46.84% |
| AH284 Rep 2 | Pancreatic Cancer | $Kras^{G12D}$, $Tp53^{lox/+}$ | 16,948,693 | 10.15% | 49.54% |
| AH284-2* | Pancreatic Cancer | $Kras^{G12D}$, $Tp53^{lox/+}$ | 1,613,592 | 48.67% | 4.78% |
| AH287 | Pancreatic Cancer | $Kras^{G12D}$, $Tp53^{lox/+}$ | 2,227,850 | 54.70% | 0.07% |
| AH288 | Pancreatic Cancer | $Kras^{G12D}$, $Tp53^{lox/+}$ | 6,780,821 | 26.57% | 14.79% |
| AH291 | Pancreatic Cancer | $Kras^{G12D}$, $Tp53^{lox/+}$ | 1,388,906 | 43.12% | 1.22% |
| AH294 | Pancreatic Cancer | $Kras^{G12D}$, $Tp53^{lox/+}$ | 969,896 | 37.20% | 3.73% |
| AH323 | Pancreatic Cancer | $Kras^{G12D}$, $SMAD4^{lox/lox}$ | 1,887,663 | 72.73% | 0.29% |
| AH346 | Pancreatic Cancer | $Kras^{G12D}$, $SMAD4^{lox/lox}$ | 1,291,648 | 32.92% | 6.07% |
| AH347 | Pancreatic Cancer | $Kras^{G12D}$, $SMAD4^{lox/lox}$ | 1,634,314 | 38.94% | 8.59% |
| AH348 | Pancreatic Cancer | $Kras^{G12D}$, $SMAD4^{lox/lox}$ | 2,030,197 | 45.84% | 5.61% |
| Colon 1 | Colon Cancer - 1 | $Kras^{G12D}$, $APC^{lox/lox}$ | 2,954,930 | 77.49% | 0.07% |
| Colon 1 | Colon Cancer - 2 | $Kras^{G12D}$, $APC^{lox/lox}$ | 985,510 | 53.13% | 6.27% |
| Colon 1 | Colon Cancer - 3 | $Kras^{G12D}$, $APC^{lox/lox}$ | 1,017,319 | 30.71% | 16.02% |
| KN2128 | Lung Cancer | $Kras^{G12D}$, $Tp53^{lox/lox}$ | 2,233,183 | 60.78% | 2.66% |
| KN2199 | Lung Cancer | $Kras^{G12D}$, $Tp53^{lox/lox}$ | 1,653,948 | 43.21% | 5.37% |
| AH323 | PDAC Cell Line | $Kras^{G12D}$, $SMAD4^{lox/lox}$ | 1,958,108 | 83.13% | 0.02% |
| AH324 | PDAC Cell Line | $Kras^{G12D}$, $Tp53^{lox/+}$ | 3,301,108 | 86.32% | 0.04% |
| NB490 | PDAC Cell Line | $Kras^{G12D}$, $Tp53^{lox/lox}$ | 15,378,802 | 76.85% | 0.03% |
| AH284 Rep 1 | Matched Normal Liver | $Kras^{G12D}$, $Tp53^{lox/+}$ | 2,270,669 | 75.68% | 0.40% |
| AH284 Rep 2 | Matched Normal Liver | $Kras^{G12D}$, $Tp53^{lox/+}$ | 1,627,749 | 56.59% | 0.34% |
| AH284-2* | Matched Normal Liver | $Kras^{G12D}$, $Tp53^{lox/+}$ | 644,316 | 41.10% | 0.31% |
| Colon 1 | Matched Normal Liver | $Kras^{G12D}$, $APC^{lox/lox}$ | 1,536,346 | 86.53% | 0.02% |
| Normal 1 | Normal Pancreas | WT | 247,582 | 14.49% | 0.41% |
| Normal 2 | Normal Pancreas | WT | 244,719 | 11.15% | 0.41% |

Figure 1B:
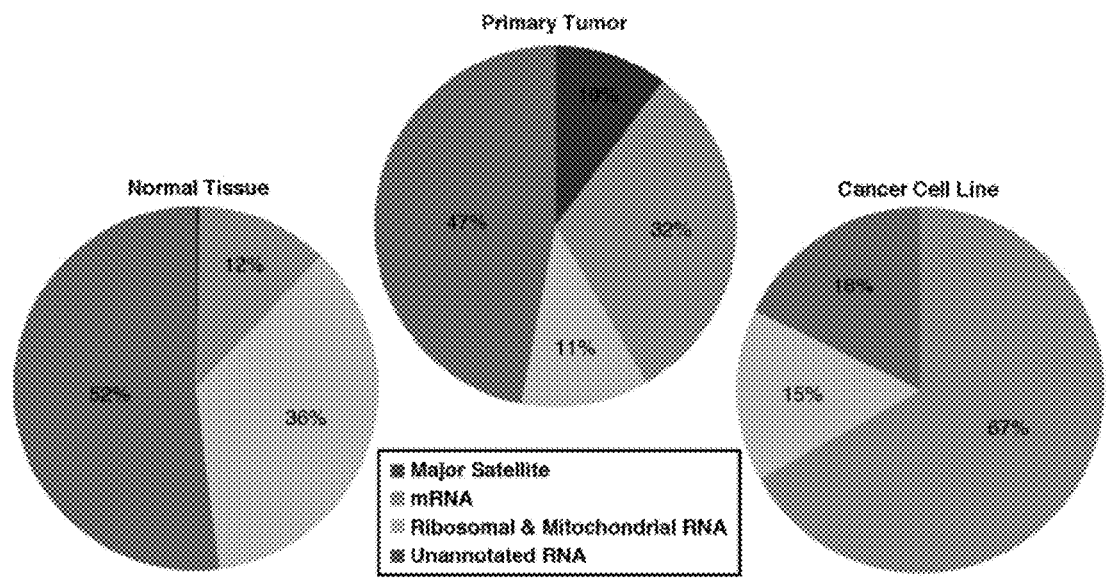
FIG. 1B is a graphical representation of sequence read contributions from major satellite among all primary tumors, cancer cell lines, and normal tissues.

*AH284-2 was RNA extraction from a different part of the pancreatic tumor and liver Of note, the composite distribution of all RNA reads among coding, ribosomal and other non-coding transcripts showed significant variation between primary tumors and normal tissues (FIG. 1A), suggesting that the global cellular transcriptional machinery is affected by the massive expression of satellite transcripts in primary tumors. Immortalized cell lines established from 3 primary pancreatic tumors displayed minimal expression of satellite repeats, suggesting either negative selection pressure during in vitro proliferation or reestablishment of stable satellite silencing mechanisms under in vitro culture conditions (FIG. 1A). Of note in primary tumors overexpressing satellites, the composite distribution of all RNA reads among coding, ribosomal and other non-coding transcripts shows significant variation with that of normal tissues (FIG. 1B), suggesting that the cellular transcriptional machinery is affected by the massive expression of satellite transcripts in these tumors.

Example 2. Major Satellite Transcripts are of Various Sizes Depending on Tissue Type and Expression Levels are Linked to Genomic Methylation and Amplification Northern blot analysis of mouse primary pancreatic tumors was carried out as follows. Northern Blot was performed using the NorthernMax-Gly Kit (Ambion). Total RNA (10 ug) was mixed with equal volume of Glyoxal Load Dye (Ambion) and incubated at 50° C. for 30 min. After electrophoresis in a 1% agarose gel, RNA was transferred onto BrightStar-Plus membranes (Ambion) and crosslinked with ultraviolet light. The membrane was prehybridized in ULTRAhyb buffer (Ambion) at 68° C. for 30 min. The mouse RNA probe (1100 bp) was prepared using the MAXIscript Kit (Ambion) and was nonisotopically labeled using the BrightStar Psoralen-Biotin Kit (Ambion) according to the manufacturer's instructions. Using 0.1 nM probe, the membrane was hybridized in ULTRAhyb buffer (Ambion) at 68° C. for 2 hours. The membrane was washed with a Low Stringency wash at room temperature for 10 min, followed by two High Stringency washes at 68° C. for 15 min. For nonisotopic chemiluminescent detection, the BrightStar BioDetect Kit was used according to the manufacturer's instructions.

Figures 2A, 2B:
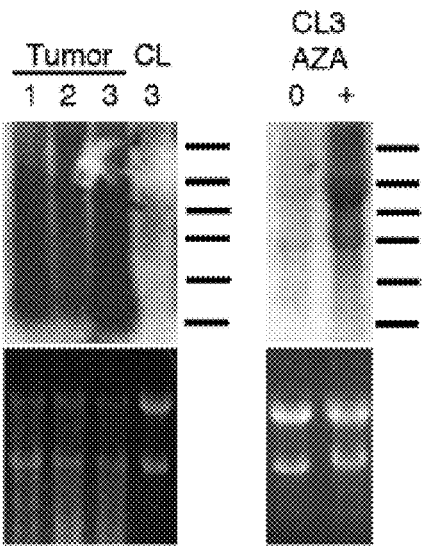
FIG. 2A shows the results of Northern blot analysis of three KrasG12D, Tp53lox/+ pancreatic primary tumors (Tumors 1-3) and a stable cell line (CL3) derived from Tumor 3.
FIG. 2B shows the results of Northern blot analysis of CL3 before (0) and after (+) treatment with the DNA hypomethylating agent 5-azacitadine (AZA).
Figure 2C:
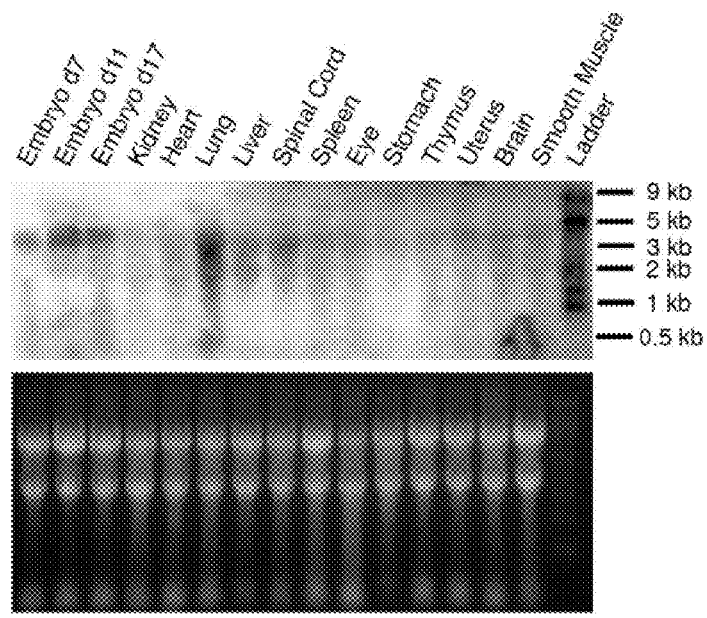
FIG. 2C shows the results of Northern blot analysis of total RNA from multiple adult and fetal mouse tissues. All Northern blots exposed for approximately 30 minutes.
Figure 2D:
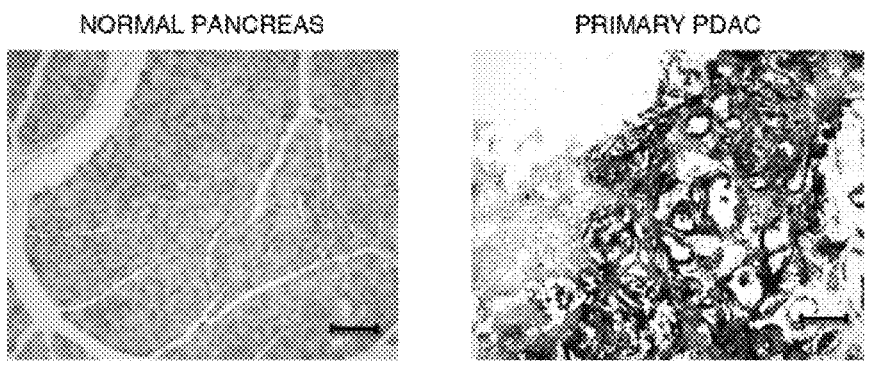
FIG. 2D is a pair of photomicrographs showing the results of RNA in-situ hybridization (ISH) of normal pancreas (left) and primary pancreatic ductal adenocarcinoma (right), hybridized with a 1 kb major satellite repeat probe.
Figure 2E:
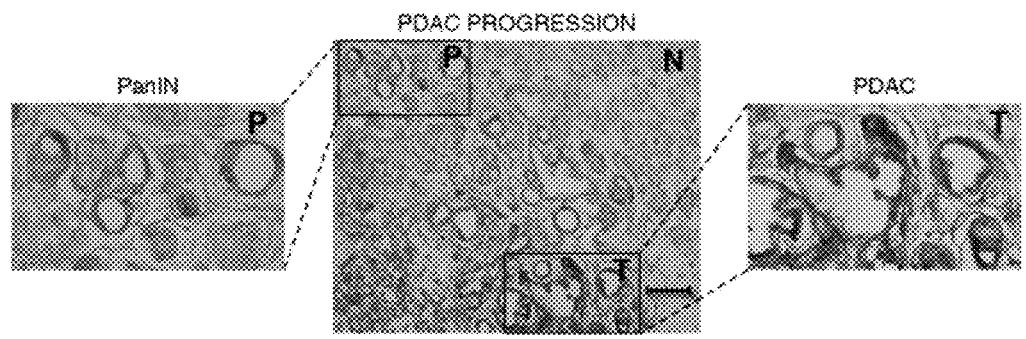
FIG. 2E is a set of three photomicrographs showing the results of ISH analysis of preneoplastic PanIN (P) lesion, adjacent to PDAC (T) and normal pancreas (N), showing positive staining in PanIN, with increased expression in full carcinoma. Higher magnification (40×) of PanIN (left) and PDAC (right) lesions.
Figure 2F:
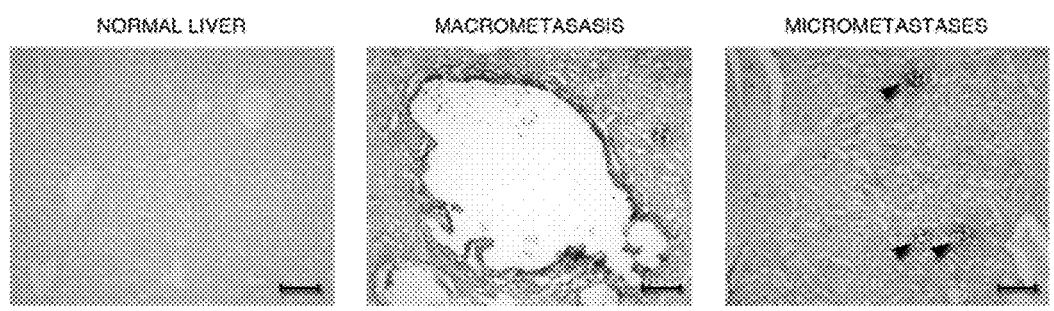
FIG. 2F is a set of three photomicrographs showing marked expression of satellites in PDAC cells metastatic to liver, which itself does not express satellites (left). Large, glandular metastatic tumor deposits are readily identified by standard histological evaluation and stain for satellite (middle). Satellite ISH is sensitive enough to detect micrometastases in liver parenchyma not easily appreciated by standard histological analysis (right; arrowheads). All images at 20× magnification (scale bar=100 μm).

The results demonstrated that the major satellite-derived transcripts range from 100 bp to 2.5 kb (FIG. 2A), consistent with the predicted cleavage of a large primary transcript comprised of multiple tandem repeats by Dicer1 (C. Kanellopoulou et al., Genes Dev 19, 489 (Feb. 15, 2005); T. Fukagawa et al., Nat Cell Biol 6, 784 (August, 2004); H. Bouzinba-Segard, A. Guais, C. Francastel, Proc Natl Acad Sci USA 103, 8709 (Jun. 6, 2006)), whose expression is 2.6-fold higher (p=0.0006, t-test) in mouse pancreatic tumors with satellite expression above the median. An established pancreatic cancer cell line derived from a primary tumor with high satellite expression has very little satellite expression confirming our sequencing results (T3 and CL3; FIG. 2A). Treatment of CL3 with 5-azacytidine leads to massive reexpression of satellite transcripts supporting DNA methylation as a mechanism for stable satellite silencing in vitro (FIG. 2B). Most normal adult mouse tissues, with the exception of lung, show minimal expression of satellite repeats (FIG. 2B). However, expression of the uncleaved 5 kb satellite transcript is evident in embryonic tissues (FIG. 2C). Thus, the aberrant expression of satellite repeats in primary pancreatic tumors does not simply recapitulate an embryonic cell fate, but also reflects altered processing of the primary 5 kb satellite transcript. The single molecule sequencing platform was exceptionally sensitive for quantitation of small repetitive ncRNA fragments, each of which is scored as a unique read. High level expression of the mouse major satellite was evident in all cells within the primary tumor (FIG. 2D), as shown by RNA in situ hybridization (ISH). Remarkably, expression was already elevated in early preneoplastic lesions, pancreatic intraepithelial neoplasia (PanIN), and it increased further upon transition to full pancreatic adenocarcinoma (FIG. 2E). Clearly defined metastatic lesions to the liver ware strongly positive by RNA ISH, as were individual PDAC cells within the liver parenchyma that otherwise would not have been detected by histopathological analysis (FIG. 2F). Low level diffuse expression was evident in liver and lung, as shown by whole mount embryo analysis, but no normal adult or embryonic tissues demonstrated satellite expression comparable to that evident in tumor cells.

To determine whether genomic amplification of satellite repeats also contributes toward the exceptional abundance of these transcripts in mouse pancreatic tumors, the index AH284 tumor was analyzed using next generation DNA digital copy number variation (CNV) analysis as described above for genomic DNA sequencing.

The results, shown in Table 3, indicated that satellite DNA comprised 18.8% of all genome-aligned reads in this tumor, compared with 2.3% of genomic sequences in matched normal liver. The major satellite repeat has previously been estimated at approximately 3% of the normal mouse genome (J. H. Martens et al., EMBO J 24, 800 (Feb. 23, 2005)). Thus, in this tumor with >100-fold increased expression of satellite repeats, approximately 8-fold gene amplification of the repeats may contribute to their abnormal expression.

TABLE 3

CNV analysis of index pancreatic tumor and normal liver from mouse AH284. Major satellite reads as a percentage of all genomic aligned reads (last column)

|  | Major Satellite Reads | Total Genomic Reads |
| --- | --- | --- |
| AH284 Liver | 183,327 (2.3%) | 7,995,538 |
| AH284 PDAC | 2,283,436 (18.8%) | 12,124,201 |

Example 3. Overexpression of Satellite Transcripts in Human Pancreatic Cancer and Other Epithelial Cancers To test whether human tumors also overexpress satellite ncRNAs, we extended the DGE analysis to specimens of human pancreatic cancer. Human pancreatic tumor tissues were obtained as excess discarded human material per IRB protocol from the Massachusetts General Hospital. Gross tumor was excised and fresh frozen in liquid nitrogen prior to nucleic acid extraction. Normal pancreas RNA was obtained from two commercial vendors, Clontech and Ambion. The samples were prepared and analyzed as described above in Example 1.

Figure 3A:
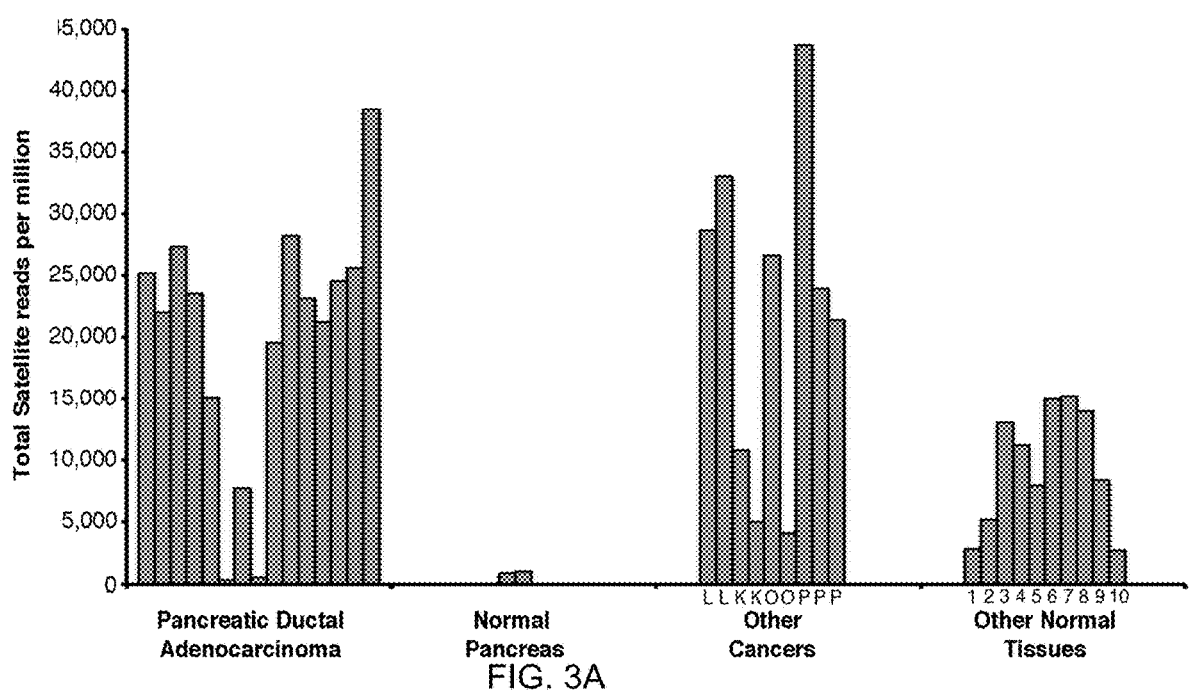
FIG. 3A is a bar graph showing the Total satellite expression in human pancreatic ductal adenocarcinoma (PDAC), normal pancreas, other cancers (L—lung, K—kidney, O—ovary, P—prostate), and other normal human tissues (1—fetal brain, 2—brain, 3—colon, 4—fetal liver, 5—liver, 6—lung, 7—kidney, 8—placenta, 9—prostate, and 10—uterus) quantitated by DGE. Satellite expression is shown as transcripts per million aligned to human genome.

Analysis of 15 PDACs showed a median 21-fold increased expression of total satellite transcripts compared with normal pancreas. A cohort of non-small cell lung cancer, renal cell carcinoma, ovarian cancer, and prostate cancer also had significant levels of satellites and the HSATII satellite. Other normal human tissues, including fetal brain, brain, colon, fetal liver, liver, lung, kidney, placenta, prostate, and uterus have somewhat higher levels of total satellite expression (Table 4, FIG. 3A).

TABLE 4

| SAMPLE ID | Genome | Total Satellite (tpm) | ALR (tpm) | HSATII (tpm) |
|---|---|---|---|---|
| PDAC 1 | 4,472,810 | 25,209 | 14,688 | 3,589 |
| PDAC 2 | 1,668,281 | 22,001 | 12,653 | 3,295 |
| PDAC 3 | 5,211,399 | 27,366 | 15,921 | 5,057 |
| PDAC 4 | 1,649,041 | 23,556 | 13,428 | 3,167 |
| PDAC 5 | 239,483 | 15,095 | 8,259 | 509 |
| PDAC 6 | 1,520,470 | 374 | 195 | 14 |
| PDAC 7 | 1,449,321 | 7,738 | 4,400 | 750 |
| PDAC 8 | 1,950,197 | 574 | 316 | 9 |
| PDAC 9 | 3,853,773 | 19,572 | 12,563 | 1,731 |
| PDAC 10 | 2,748,850 | 28,225 | 18,767 | 2,489 |
| PDAC 11 | 2,848,599 | 23,163 | 14,634 | 2,589 |
| PDAC 12 | 3,723,326 | 21,243 | 12,940 | 2,122 |
| PDAC 13 | 1,834,743 | 24,549 | 15,342 | 3,150 |
| PDAC 14 | 2,481,332 | 25,650 | 18,016 | 2,564 |
| PDAC 15 | 1,752,081 | 38,514 | 25,899 | 5,210 |
| Normal Pancreas 1 | 1,196,372 | 908 | 284 | 0 |
| Normal Pancreas 2 | 975,676 | 1,043 | 303 | 0 |
| Lung Cancer 1 | 1,549,237 | 28,658 | 18,751 | 4,417 |
| Lung Cancer 2 | 13,829,845 | 33,030 | 26,143 | 2,555 |
| Kidney Cancer 1 | 2,104,859 | 10,814 | 6,505 | 1,501 |
| Kidney Cancer 2 | 4,753,409 | 5,025 | 2,739 | 625 |
| Ovarian Cancer 1 | 12,596,542 | 26,658 | 14,513 | 3,074 |
| Ovarian Cancer 2 | 7,290,000 | 4,089 | 2,058 | 403 |
| Prostate Cancer 1 | 3,376,849 | 43,730 | 22,244 | 9,793 |
| Prostate Cancer 2 | 12,052,244 | 23,947 | 14,201 | 3,209 |
| Prostate Cancer 3 | 3,631,148 | 21,411 | 12,390 | 2,804 |
| Normal Fetal Brain | 384,453 | 2,843 | 1,516 | 3 |
| Normal Brain | 371,161 | 5,184 | 2,573 | 3 |
| Normal Colon | 183,855 | 13,059 | 7,229 | 5 |
| Normal Fetal Liver | 147,977 | 11,218 | 5,879 | 7 |
| Normal Liver | 117,976 | 7,968 | 3,730 | 25 |
| Normal Lung | 208,089 | 15,027 | 7,857 | 5 |
| Normal Kidney | 144,173 | 15,218 | 8,094 | 7 |
| Normal Placenta | 207,929 | 13,990 | 7,815 | 0 |
| Normal Prostate | 263,406 | 8,409 | 2,228 | 19 |
| Normal Uterus | 477,480 | 2,702 | 1,395 | 2 |

Figure 3B:
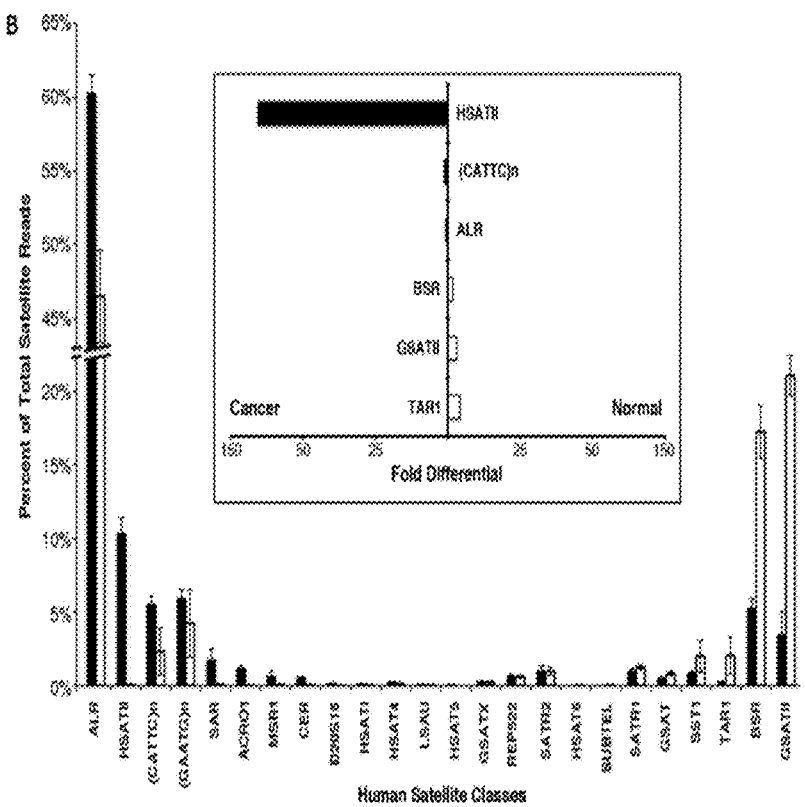
FIG. 3B is a bar graph showing a breakdown of satellite repeat classes as percent of total satellites in human PDAC (Black, n=15) and normal human tissues (White, n=12) sequenced. Satellites are ordered from highest absolute difference in tumors to highest in normal tissue (left to right). Error bars represents standard error of the mean. Fold differential of top three cancer (left, black bars) and normal (right, white bars) tissue satellite classes shown (Bar graph, center).

Subdivision of human satellite among the multiple classes revealed major differences between tumors and all normal tissues. While mouse satellite repeats are broadly subdivided into major and minor satellites, human satellites have been classified more extensively. Of all human satellites, the greatest expression fold differential is evident for the pericentromeric satellite HSATII (mean 2,416 tpm; 10.3% of satellite reads), which is undetectable in normal human pancreas (FIG. 3B). In contrast, normal tissues have much higher representation of GSATII, Beta satellite (BSR), and TAR1 classes (21.1%, 17.3%, and 2.1% of all satellite reads respectively), while these constitute a small minority of satellite reads in pancreatic cancers.

The most abundant class of normally expressed human satellites, alpha (ALR) (Okada et al., Cell 131, 1287 (Dec. 28, 2007)) is expressed at 294 tpm in normal human pancreas, but comprises on average 12,535 tpm in human pancreatic adenocarcinomas (43-fold differential expression; 60.3% of satellite reads). Thus, while the overexpression of human ALR repeats is comparable to that of mouse major satellite repeats, it is the less abundant HSATII (49-fold above GAPDH), which shows exceptional specificity for human PDAC. The co-expression of LINE-1 with satellite transcripts in human pancreatic tumors is also striking, with a mean 16,089 tpm (range 358-38,419).

Beyond ALR repeats, the satellite expression profile of normal pancreas and PDAC are strikingly different; for instance normal pancreatic tissue has a much higher representation of GSATII, TAR1 and SST1 classes (26.4%, 10.6%, and 8.6% of all satellite reads), while these were a small minority of satellite reads in pancreatic cancers. In contrast, cancers express high levels of HSATII satellites (4,000 per $10^6$ transcripts; 15% of satellite reads), a subtype whose expression is undetectable in normal pancreas (FIG. 3B). Quantitative comparison of satellite transcription in mouse versus human pancreatic cancers shows that mouse major satellites are expressed a median 466-fold above the abundant Gapdh mRNA, while the human ALR and HSATII satellites are respectively expressed 180-fold and 47-fold above GAPDH.

Example 4. Cellular Transcripts with Linear Correlation to Increasing Satellite Levels are Enriched for Stem Cell and Neural Elements that is Linked to Histone Demethylases and RNA Processing Enzymes The generation of comprehensive DGE profiles for 25 different mouse tissues of different histologies and genetic backgrounds made it possible to correlate the expression of cellular transcripts with that of satellites across a broad quantitative range. To identify such co-regulated genes, all annotated transcripts quantified by DGE were subjected to linear regression analysis, and transcripts with the highest correlation coefficients to satellite expression were rank ordered.

All mouse sample reads were aligned to a custom made library for the mouse major satellite (sequence from UCSC genome browser). Human samples were aligned to a custom made reference library for all satellite repeats and LINE-1 variants generated from the Repbase library (Pushkarev et al., Nat Biotech 27, 847 (2009)). In addition, all samples were subjected to the DGE program for transcriptome analysis. Reads were normalized per $10^6$ genomic aligned reads for all samples.

For linear correlation of mouse major satellite to transcriptome, all tissues and cell lines were rank ordered according to level of major satellite. All annotated genes were then subjected to linear regression analysis across all tissues. Genes were then ordered according to the Pearson coefficient for linear regression and plotted by Matlab.

Figure 4A:
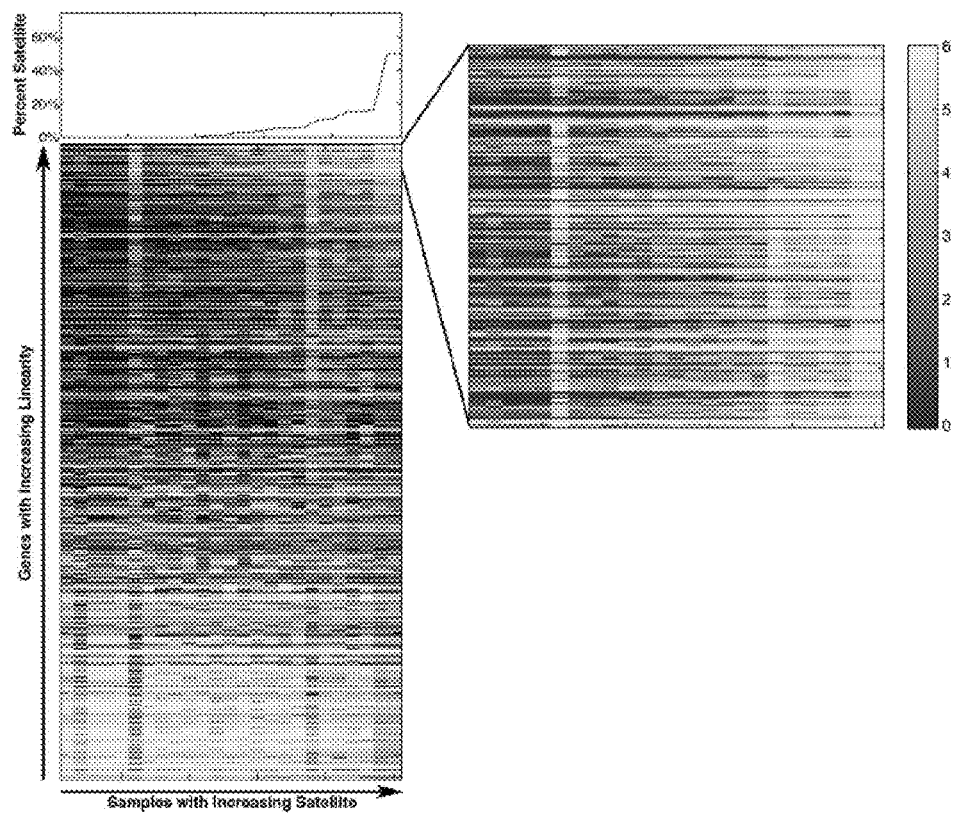
FIG. 4A shows the results of multiple linear correlation analysis of major satellite to other cellular transcripts among all mouse tumors and normal tissues as depicted by a heat map. X-axis is samples ordered by expression of major satellite and y-axis is genes ordered by linear correlation to major satellite expression. Light grey (High) and dark grey (Low) color is log 2 (reads per million). Major satellite expression as percent genomic aligned reads (y-axis) rank ordered by satellite reads (x-axis) with expanded view of top genes with highest linearity (R≥0.85) with satellite levels.

Analysis of a set of 297 genes with highest linear correlation (R>0.85) revealed 190 annotated cellular mRNAs and a subset of transposable elements (FIG. 4A).

Of all transcripts analyzed with high linear correlation, the autonomous retrotransposon Line-1 had the highest expression level in mouse samples of diverse tissue types. Mouse pancreatic tumors have a mean Line-1 expression 30,690 tpm (range 183-120,002), representing an average of 330-fold higher levels compared to Gapdh (Table 5).

TABLE 5

| | Normalized Reads per $10^6$ transcripts | |
|---|---|---|
| | LINE-1 | GAPDH |
| Mouse PDAC | 30,690 (183-120,002) | 171 (19-417) |
| Human PDAC | 6,091 (5,153-6,921) | 48 (26-67) |

The co-expression of LINE-1 with satellite transcripts in human pancreatic tumors was also striking, with an average of 6,091 per $10^6$ transcripts (127-fold higher than GAPDH). Increased expression of the Tigger transposable elements 3 and 4 were also correlated with increasing satellite transcription in mouse tumors, but was not seen human tumors.

In addition to retroelements, a subset of cellular mRNAs showed a very high degree of correlation with the levels of satellite repeat expression across diverse mouse tumors (referred to herein as "Satellite Correlated Genes (SCGs)"). Linearly correlated genes with R>0.85 were mapped using the DAVID program (Dennis, Jr. et al., Genome Biol 4, P3 (2003); Huang et al., Nat Protoc 4, 44 (2009)). These genes were then analyzed with the Functional Annotation clustering program and the UP TISSUE database to classify each of these mapped genes. Germ/Stem cell genes included genes expressed highly in testis, egg, trophoblast, and neural stem cells. Neural genes included genes expressed highly in brain, spinal cord, and specialized sensory neurons including olfactory, auditory, and visual perception. HOX and Zinc Finger proteins were classified using the INTERPRO database.

Analysis of 190 annotated transcripts using the DAVID gene ontology program identified 120 (63%) of these transcripts as being associated with neural cell fates and 50 (26%) linked with germ/stem cells pathways (Table 6).

TABLE 6

|  | Germ/Stem Cell | Neural | HOX Region | Zinc Finger Domain |
| --- | --- | --- | --- | --- |
| TOTAL COUNTS | 50 | 120 | 10 | 16 |
| % Mapped (190) | 26% | 63% | 5% | 8% |

Figure 4B:
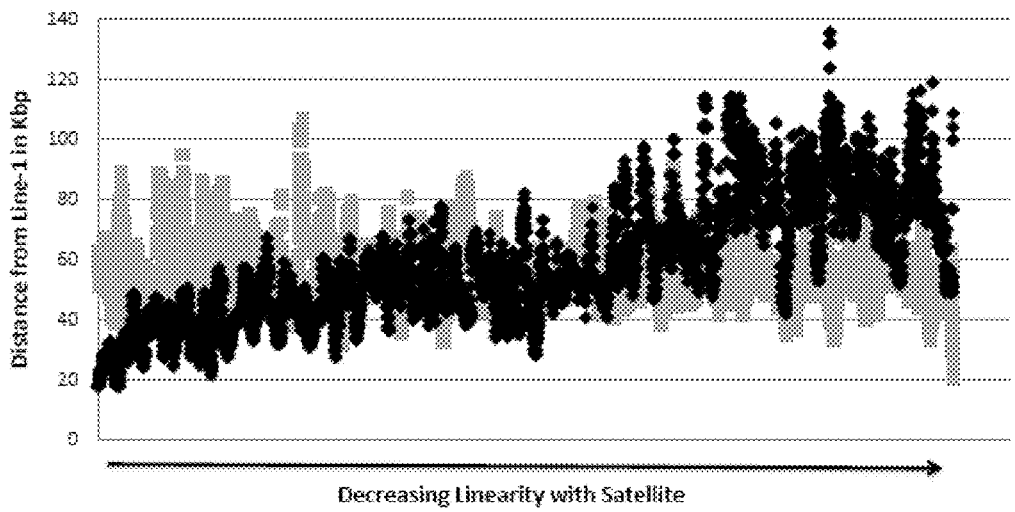
FIG. 4B is a dot graph showing the Median distance of transcriptional start sites of all genes to Line-1 elements ordered by linearity to satellite expression (Dark gray; highest linearity to the left) or by random (Light gray). Plotted by genes binned in 100s.

In addition, significant enrichment was evident for transcriptional regulators, including HOX related (9, 5%) and zinc finger proteins (16, 8%). This gene set could not be matched to any known gene signature in the GSEA database (Subramanian et al., Proc Natl Acad Sci USA 102, 15545 (Oct. 25, 2005)), but the ontology analysis points towards a neuroendocrine phenotype. Neuroendocrine differentiation has been described in a variety of epithelial malignancies, including pancreatic cancer (Tezel et al., Cancer 89, 2230 (Dec. 1, 2000)), and is best characterized in prostate cancer where it is correlated with more aggressive disease (Cindolo et al., Urol Int 79, 287 (2007)). A striking increase in the number of carcinoma cells staining for the characteristic neuroendocrine marker chromogranin A, as a function of higher satellite expression in mouse PDACs (FIG. 4D), was observed, supporting the link between globally altered expression of ncRNAs and a specific cellular differentiation program.

SCGs were more readily identified in mouse tumors, since the large dynamic range in major satellite expression enabled linear correlation in expression level between satellites and protein-encoding genes. However, human orthologs were identified for 138 of the 190 annotated mouse SGCs, of which 54 (39%) showed >2-fold increased expression in human PDACs compared with normal pancreas (q-value<0.1). Together, these observations suggest that, as in the mouse genetic model, tumor-associated derepression of satellite-derived repeats is highly correlated with increased expression of Line-1 and a subset of cellular mRNAs.

Histone modifications, including H3K9 trimethylation (P. A. Cloos, J. Christensen, K. Agger, K. Helin, Genes Dev 22, 1115 (May 1, 2008)), combined with Dicer1 and Piwi-related protein-mediated ncRNA processing (A. A. Aravin, G J. Hannon, J. Brennecke, Science 318, 761 (Nov. 2, 2007)) have been linked to maintenance of repression of satellite repeats. To search for candidate regulators of satellite derepression in primary tumor specimens, we first measured the quantitative DGE of known epigenetic regulators and RNA processing genes in mouse tumors, as a function of increasing major satellite expression.

A targeted gene expression analysis of demethylases and RNA processing enzymes was carried out in mouse and human PDAC samples. A list of demethylases and RNA processing enzymes were generated from two recent publications (Cloos et al., Genes Dev 22, 1115 (2008); Aravin et al., Science 318, 761 (2007)). Mouse PDACs with $Kras^{G12D}$ and Tp53 loss were used for this analysis. Mouse tumors were separated into high vs low satellite levels using the median satellite expression (7%). A total of 37 genes were evaluated between high and low satellite tumors and fold change was calculated. Analysis of the population means was compared using the 2-tailed student t-test assuming equal variance. Genes that had a significance value of p<0.05 (total of 7 gene) were then used to evaluate human PDAC versus human normal pancreatic tissue. Fold change and a 2-tailed student t-test with equal variance was then applied to human PDAC vs normal pancreatic tissue to find potential gene candidates involved with satellite expression.

Among 37 candidate genes tested, mouse pancreatic tumors with satellite expression above the median had higher expression of the demethylases Hspbap1, Jmjd1B, Jmjd4, Jarid1d, Jmjd3, and Fbxl10 as well as the RNA processing enzyme Dicer1. Among these, HSPBAP1, FBXL10 and DICER1 overexpression was also observed in human pancreatic adenocarcinomas (Table 7, p<0.05, student t-test).

TABLE 7

List of candidate demethylases and RNA processing enzymes identified in mouse PDAC tumors compared to human PDAC.

| GENE NAME | Mouse PDAC High vs Low Satellite | | Human PDAC vs Normal Panc | |
| --- | --- | --- | --- | --- |
|  | FOLD Expression | T-test p-value | FOLD Expression | T-test p-value |
| HSPBAP1 | 5.11 | 0.0005 | 11.59 | 0.0069 |
| DICER1 | 2.56 | 0.0006 | 3.00 | 0.0023 |
| JMJD1B (KDM3B) | −2.16 | 0.0010 | 1.16 | 0.8051 |
| JMJD4 | 3.10 | 0.0021 | 1.18 | 0.8080 |
| JARID1D (SMCY, KDM5D) | 9.84 | 0.0031 | 1.62 | 0.7107 |
| JMJD3 (KDM6B) | 1.62 | 0.0118 | 3.02 | 0.1109 |
| FBXL10 (KDM2B) | 1.40 | 0.0412 | 7.96 | 0.0279 |

Demethylases and RNA processing enzymes enriched in high vs low major satellite expressing mouse tumors (First two columns) ordered by highest significance (lowest p-value). Human PDAC vs normal tissue fold change and t-test p-value shown for each of these genes (Last two columns). Genes differentially expressed in both human and mouse tumors with a significance value of p < 0.05 are highlighted in bold.

The catalytic activity of HSPBAP1 and FBXL10 demethylases has not been extensively characterized, although the former is noteworthy for its contribution to the familial renal cancer DIRC3-HSPBAP1 fusion (D. Bodmer, M. Schepens, M. J. Eleveld, E. F. Schoenmakers, A. Geurts van Kessel, Genes Chromosomes Cancer 38, 107 (October, 2003)) and the latter appears to have some specificity for H3K36me2/me1 and H3K4me3, with an effect on ribosomal RNA expression and cellular proliferation (D. Frescas, D. Guardavaccaro, F. Bassermann, R. Koyama-Nasu, M. Pagano, Nature 450, 309 (Nov. 8, 2007)). While current understanding of multicomponent chromatin modifier complexes precludes linking satellite and Line-1 upregulation in primary tumors with aberrant expression of a single transcript, the relatively small number of genes with consistently altered expression may point to a key subset of epigenetic regulators that contribute to satellite and Line-1 derepression.

While failure of a common transcriptional silencing mechanism may contribute to repression of LINE-1 and satellite repeats, the diverse array of cellular transcripts whose overexpression is correlated with these repetitive sequences is less readily explained. Of note, recent findings have demonstrated that LINE-1 may drive expression of specific cellular mRNAs through its insertion upstream of their transcriptional start sites (T. Kuwabara et al., Nat Neurosci 12, 1097 (September, 2009)) or through alterations in flanking chromatin marks (J. A. Bailey, L. Carrel, A. Chakravarti, E. E. Eichler, Proceedings of the National Academy of Sciences of the United States of America 97, 6634 (Jun. 6, 2000, 2000); D. E. Montoya-Durango et al., Mutat Res 665, 20 (Jun. 1, 2009)). To test whether such a mechanism might also underlie the co-expression of the 297 cellular mRNAs identified here, we analyzed the genomic distance between their transcriptional start site and LINE-1 insertions in the genome.

The transcriptional start sites tissues and cell lines were determined (UCSC genome browser (D. Karolchik et al., Nucleic Acids Res 32, D493 (Jan. 1, 2004))) as well as the position of all Line-1 elements in the mouse genome with a threshold of 1 Kbp in length. Line-1 closest distance upstream of the transcriptional start sites of all annotated genes with a minimum expression level of 5 transcripts per million were calculated. Genes were then rank ordered according to the Pearson coefficient for linear regression. Genes were binned in 100s and plotted by Excel. Randomization of all genes, followed by binning, and plotting was done as a control.

Focusing on the top linearly correlated genes (R>0.85), these genes were plotted as a frequency plot against distance of Line-1 elements upstream of the transcriptional start site. Enrichment was calculated at 5 Kbp and the Fisher Exact test was used to calculate the test statistic.

Figure 4C:
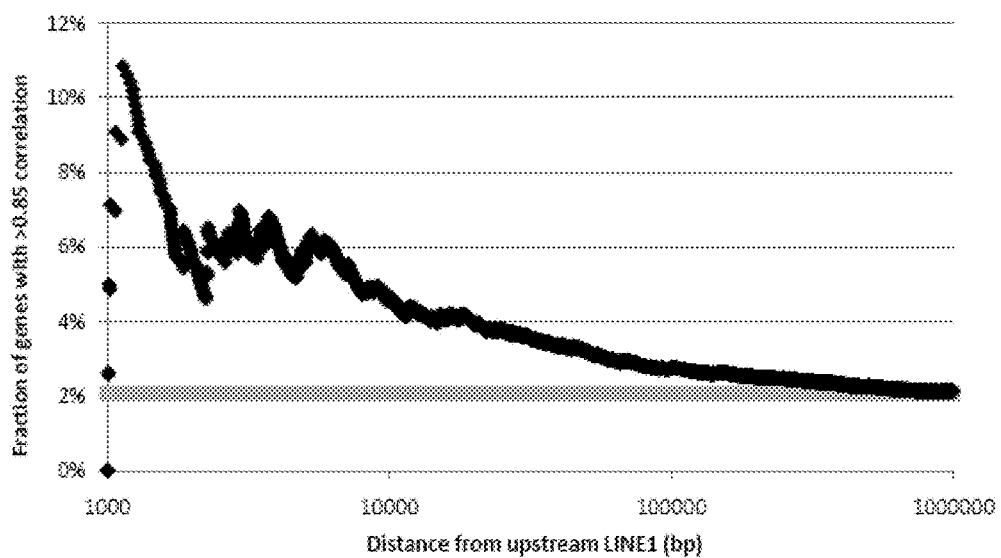
FIG. 4C is a dot graph showing Top genes with highest linearity (R>0.85) defining satellite correlated genes or SCGs plotted by frequency against distance of transcriptional start site to LINE-1 elements (Dark gray) compared to the expected frequency of these genes (Light gray).
Figure 4D:
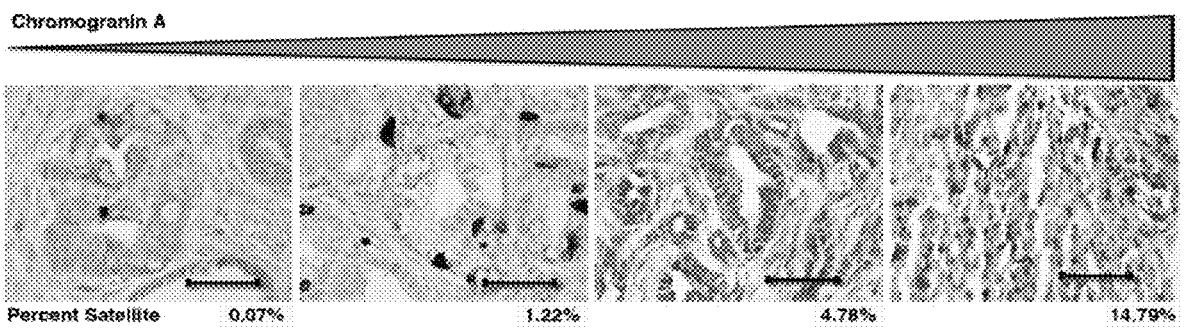
FIG. 4D is a set of four photomicrographs showing the results of immunohistochemistry of mouse PDAC (KrasG12D, Tp53 lox/+) for the neuroendocrine marker chromogranin A. Tumors are depicted as a function of increasing chromogranin A staining (dark grey), with the relative level of major satellite expression noted for each tumor at the bottom of each image (percentage of all transcripts)

Remarkably, there was a striking correlation of LINE-1 genomic distance to expression of genes with the major satellite (FIG. 4B), and there was highly significant enrichment of our top 297 genes for presence of a LINE-1 element within 5 Kbp of the transcriptional start site (Enrichment 2.69, p=8.18×10$^{-7}$, Fisher exact test, FIG. 4C).

Thus, activation of LINE-1 sequences within the proximity of cellular transcripts may contribute to their overexpression in primary tumors, in striking correlation with the expression of both LINE-1 and satellite repeats. The consequence of increased expression of these cellular transcripts remains to be defined. However, the high prevalence of genes linked to stem-like and neurogenic fates, along with the frequency of HOX and zinc finger transcriptional regulators raises the possibility that at least a subset of these may contribute to tumor-related phenotypes.

Example 5. LINE-1 is a Specific and Sensitive Marker of CTCs

Satellite levels are most strongly linked with the expression of the autonomous retrotransposon Line-1, which has recently been shown to be a major cause for genomic variation in normal and tumor tissues (J. Berretta, A. Morillon, EMBO Rep 10, 973 (September, 2009); A. Jacquier, Nat Rev Genet 10, 833 (December, 2009); M. Guenatri, D. Bailly, C. Maison, G Almouzni, J Cell Biol 166, 493 (Aug. 16, 2004)). Aberrant expression of cellular transcripts linked to stem cells and neural tissues is also highly correlated with satellite transcript levels, suggesting alteration of cell fate through derepression of a coordinated epigenetic program.

Figure 5:
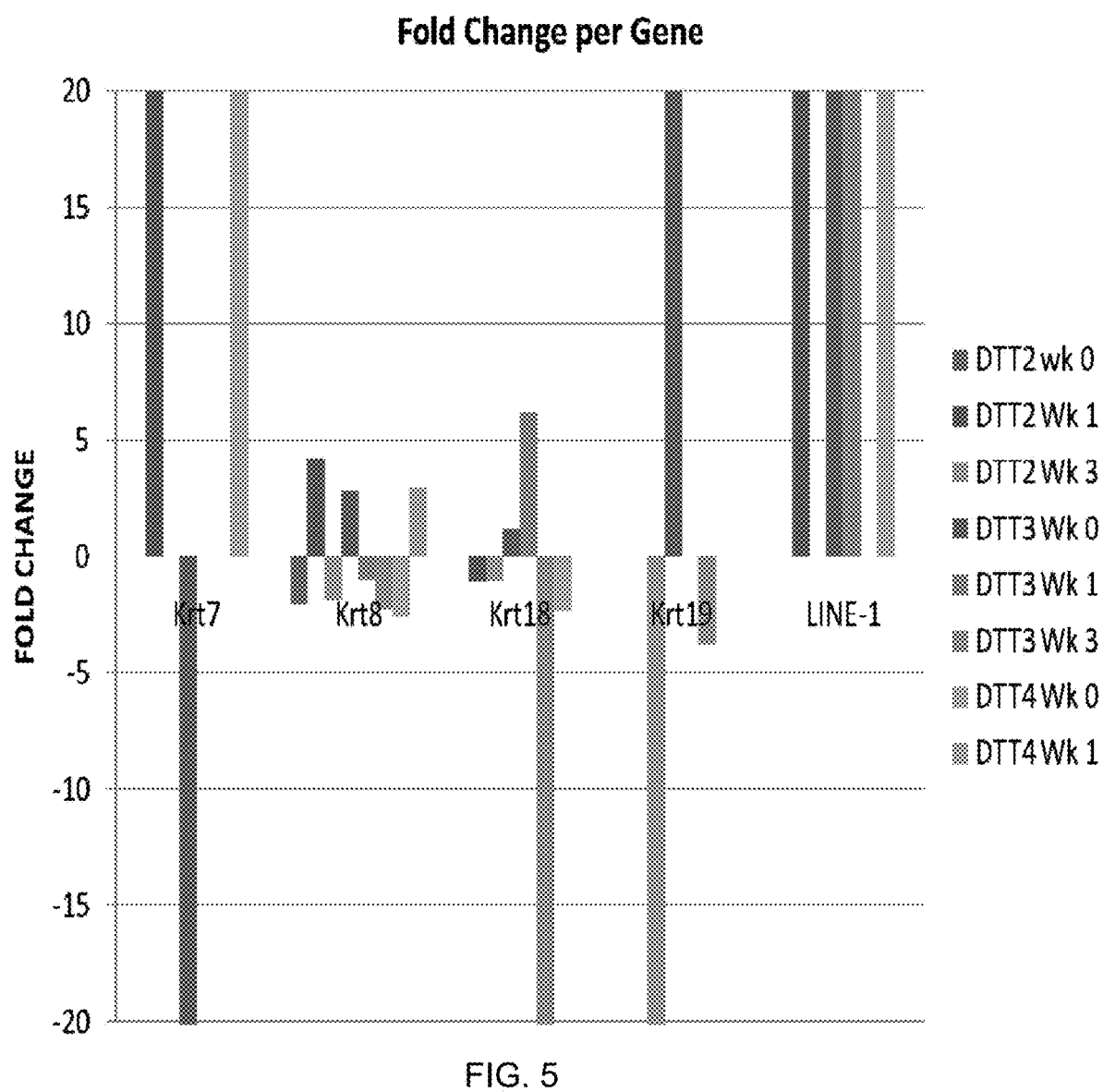
FIG. 5 is a bar graph indicating fold change expression of the indicated genes in CTC Device vs. control device. The subjects were newly diagnosed metastatic pancreatic adenocarcinoma patients. LINE-1 expression was seen in all patients at some point.

Expression of LINE-1 in circulating tumor cells (CTCs) in newly diagnosed metastatic pancreatic adenocarcinoma patients was evaluated using a CTC device known as a herringbone chip (HB), which combines specific antibody mediated capture against the epithelial cell adhesion molecule (EpCAM) and the high-throughput advantages of microfluidics (Stott et al., Proc Natl Acad Sci USA, 107 (43):18392-18397 2010). Blood was collected from cancer patients that had given consent. Approximately 3 mL of blood was processed on the CTC device and a control device over 2 hours. RNA was extracted from the devices using the Qiagen RNeasy MinElute kit. RNA was then subjected to cDNA synthesis with random primers using the Superscript III first strand synthesis kit (invitrogen). RNA was removed with RNase and cDNA was subject to qRT-PCR using Human LINE-1 Taqman assay (Applied Biosystems). LINE-1 expression was normalized to GAPDH in the CTC and control device. Fold difference between the CTC device and control device was then calculated by standard Ct calculation for qPCR. As shown in FIG. 5, LINE-1 expression was seen much more consistently and with higher frequency compared to keratins (Krt) which are typical CTC markers (S. Maheswaran et al., N Engl J Med. 359, 366 (Jul. 24, 2008); S. Nagrath et al., Nature. 450, 1235 (Dec. 20, 2007)). Preliminary data of HSATII positive cells suggests a 10 fold improvement in sensitivity of CTC detection. This demonstrates that LINE-1 is a specific and sensitive marker for detecting CTCs. The ability of satellites to increase the sensitivity of detecting pancreatic CTCs offers not only a more robust blood based diagnostic for cancer treatment monitoring, but a significant improvement in the ability to use CTCs as an early detection modality. This provides a screening tool for cancer, improving chances of early detection, which can improve the ability to provide curative therapy.

Example 6. HSATII RNA In Situ Technique Using Branched DNA Detection Technology

Figure 6A:
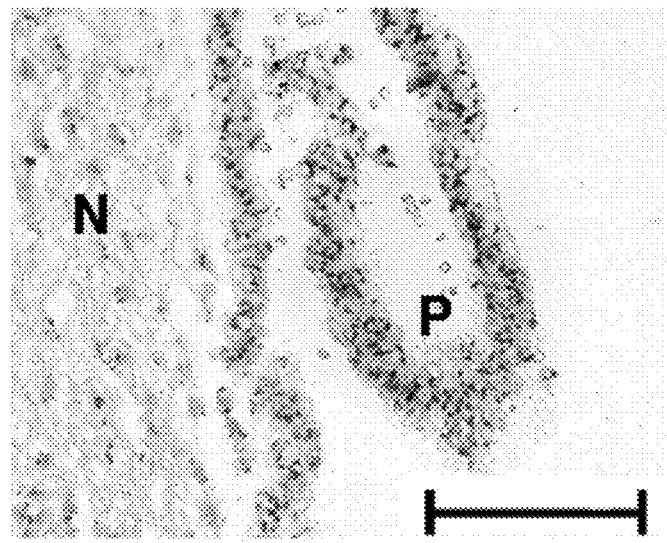
FIG. 6A is an image of RNA in situ hybridization (RNA-ISH) of human satellite HSATII in a human preneoplastic PanIN (P) lesion with adjacent non-cancerous stroma tissue (N) in formalin fixed paraffin embedded tissue (Top image) and fine needle aspirate biopsy of PDAC (T) and normal adjacent leukocytes (N). (Dark grey dots=HSATII). Scale bar=100 μm
Figure 6A:
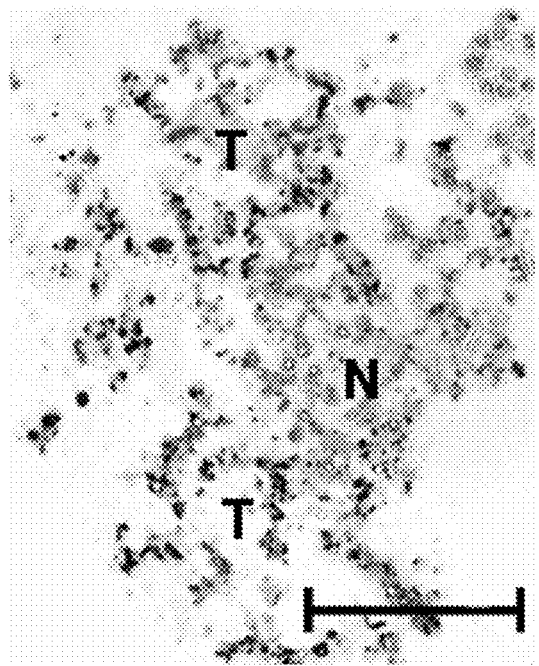
Figure 6B:
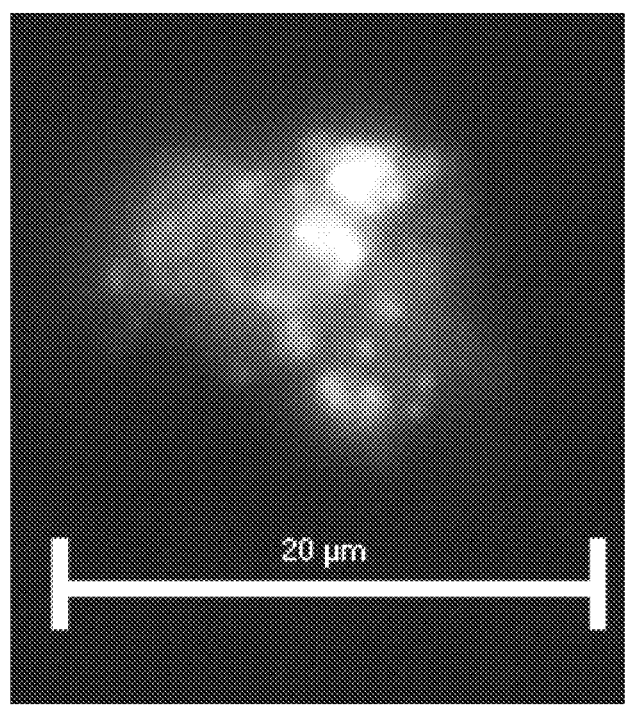
FIG. 6B is an image of RNA in situ hybridization of HSATII using Affymetrix ViewRNA of a potential human pancreatic circulating tumor cell captured on the HB-chip. HSATII (lightest areas; yellow in original), DAPI nuclear stain (medium grey areas, blue in original). Scale bar=20 μm.

As noted above, the HSATII satellite is overexpressed in pancreatic cancer and was confirmed to be overexpressed in human preneoplastic pancreatic lesions (FIG. 6A) using a branched DNA detection assay (QuantiGene® ViewRNA Assay, Affymetrix). Breast cancer samples were also tested for HSATII using this method and were found to have significant expression compared to normal breast tissues. Extension of this technique to potential circulating tumor cells captured on the HB-chip (FIG. 6B) has been accomplished indicating that HSATII may be used as a blood based diagnostic for epithelial cancers.

Example 7. Satellites Levels in Serum

Serum was extracted from the blood of 8 metastatic pancreatic cancer patients by using Ficoll buffy coat method. Serum RNA (cell free RNA), which includes exosomes, was purified using the Trizol method and then purified using Qiagen RNA MinElute columns kits. RNA was then subjected to Helicos DGE sequencing preparation and sequenced on a HeliScope next generation sequencer. Results of this data are summarized in Table 1. As described above, HSATII was specific for cancer and GSATII was found to correlate with normal tissues. Therefore the ratio of HSATII to GSATII was evaluated as a marker for identifying cancer burden and potentially an early detection marker. In this case, one patient who had stable disease had the lowest HSATII/GSATII ratio as predicted (see Table 8). These results suggest that detection of satellites in peripheral blood serum (cell free RNA) can be used as a predictive marker of disease response to therapy.

TABLE 8

Table 8: A total of 8 metastatic cancer patients with clinical status, total satellites, HSATII, and GSATII in transcripts per million aligned to genome (tpm) and the ratio of HSATII/GSATII in cell free RNA sequenced.

| Patient ID | Clinical status | Total Satellites (tpm) | HSATII (tpm) | GSATII (tpm) | HSATII/ GSATII |
|---|---|---|---|---|---|
| PDAC 3 | PROGRESSION | 43,932 | 1,576 | 4,904 | 32% |
| PDAC 6 | PROGRESSION | 21,845 | 735 | 3,151 | 23% |
| PDAC 9 | PROGRESSION | 39,235 | 1,867 | 1,857 | 101% |
| PDAC 11 | PROGRESSION | 28,817 | 784 | 3,785 | 21% |
| PDAC 12 | PROGRESSION | 2,472 | 59 | 83 | 71% |
| PDAC 16 | STABLE | 43,629 | 162 | 6,437 | 3% |
| PDAC 18 | PROGRESSION | 18,034 | 231 | 2,450 | 9% |
| PDAC 19 | PROGRESSION | 38,425 | 399 | 5,287 | 8% |

However, in a preliminary evaluation of healthy donor serum (cell free) RNA (n=4) HSATII and GSATII did not perform as well as expected, though the presence of. However, other satellites like TAR1 seemed to be better predictors of "cancer" compared to "non-cancer" status as shown in Table 9. TAR1 was significantly different between the two populations with a p value=0.025.

TABLE 9

Table 9: Average total satellites, HSATII, GSATII, HSATII/GSATII, and TAR1 (tpm) in a total of 8 metastatic PDAC patients and 4 healthy donors with cell free RNA sequenced. Student t-test was used to calculate significance.

|  | Total Satellites (tpm) | HSATII (tpm) | GSATII (tpm) | HSATII/ GSATII | TAR1 (tpm) |
|---|---|---|---|---|---|
| AVG PDAC | 29,549 | 727 | 3,494 | 0.33 | 100 |
| AVG HD | 47,279 | 6,275 | 6,081 | 1.12 | 51 |
| TTEST | 0.114 | 0.172 | 0.103 | 0.25 | 0.025 |
| FOLD | 0.625 | 0.116 | 0.575 | 0.30 | 1.963 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An in vitro method of detecting a solid tumor of epithelial origin in a subject, the method comprising:
   quantifying a level of total HSATII satellite transcripts per million transcripts in a test sample comprising cells from the subject to obtain a test value;
   quantifying a level of total HSATII satellite transcripts per million transcripts in a noncancerous reference sample comprising cells of the same cell type as the test sample;
   detecting an increase in the test value compared to the level of total HSATII satellite transcripts per million transcripts in the noncancerous reference sample, wherein the increase indicates that the subject has cancer;
   and administering to the subject a surgical intervention, chemotherapy, radiation therapy, or a combination thereof.

2. The method of claim 1, wherein the solid tumor of epithelial origin is pancreatic, lung, breast, prostate, renal, ovarian or colon cancer.

3. The method of claim 1, wherein the test value in the test sample is more than about 100 HSATII transcripts per million transcripts.

4. The method of claim 1, wherein the level of HSATII satellite transcripts in the noncancerous reference sample is less than about 20 HSATII transcripts per million transcripts.

5. The method of claim 1, wherein the step of administering comprises administering a surgical intervention.

6. The method of claim 1, wherein the step of administering comprises administering chemotherapy.

7. The method of claim 1, wherein the step of administering comprises administering radiation therapy.

8. An in vitro method of detecting pancreatic cancer in a subject, the method comprising:
   quantifying a level of total HSATII satellite transcripts per million transcripts in a test sample comprising pancreatic cells from the subject to obtain a test value;
   quantifying a level of total HSATII satellite transcripts per million transcripts in a noncancerous reference sample comprising pancreatic cells;
   detecting an increase in the test value compared to the level of total HSATII satellite transcripts per million transcripts in the noncancerous reference sample, wherein the increase indicates that the subject has pancreatic cancer;
   and administering to the subject a surgical intervention, chemotherapy, radiation therapy, or a combination thereof.

9. The method of claim 8, wherein the step of administering comprises administering a surgical intervention.

10. The method of claim 8, wherein the step of administering comprises administering chemotherapy.

11. The method of claim 8, wherein the step of administering comprises administering radiation therapy.

* * * * *

SEQUENCE LISTING

```
<160> NUMBER OF SEQ ID NOS: 8

<210> SEQ ID NO 1
<211> LENGTH: 171
<212> TYPE: DNA
<213> ORGANISM: Homo sapiens

<400> SEQUENCE: 1
aattctcagt aacttccttg tgttgtgtgt attcaactca cagagttgaa cgatcctta        60 cacagagcag acttgaaaca ctcttttgt ggaatttgca agtggagatt tcagccgctt      120
tgaggtcaat ggtagaatag gaaatatctt cctatagaaa ctagacagaa t              171

<210> SEQ ID NO 2
<211> LENGTH: 171
<212> TYPE: DNA
<213> ORGANISM: Homo sapiens

<400> SEQUENCE: 2
tcattctcag aaactrcttt gtgatgtgtg crttcaactc acagagttta accttctt        60 tgatagagca gtttggaaac actctgtttg taaagtctgc aagtggatat ttggacctct    120
ttgaggcctt cgttggaaac gggatttctt catataatgc tagacagaag a              171

<210> SEQ ID NO 3
<211> LENGTH: 179
<212> TYPE: DNA
<213> ORGANISM: Homo sapiens

<400> SEQUENCE: 3
agctttctga gaaactgctt tgtgatgtgt gcattcatct cacagagtta aacctttctt      60
ttgattcagc agtttggaaa cactgttttt gtagaatctg tgaagggata tttgggagct    120
cattgaggcc tatggtgaaa aagaaaatat cttcagataa aaactagaag gaagctatc      179
```

```
<210> SEQ ID NO 4
<211> LENGTH: 172
<212> TYPE: DNA
<213> ORGANISM: Pan troglodytes

<400> SEQUENCE: 4
ctatctgaga aactgctttg tgatgtgtgc attcatctca cagagttaaa cctttctttt      60
gattcagcag tttggaaaca ctgttttgt agaatctgcg aagggacatt tgggagctca     120
ttgaggccta tggtgaaaaa gcgaatatcc ccagataaaa actagaaaga ag            172

<210> SEQ ID NO 5
<211> LENGTH: 172
<212> TYPE: DNA
<213> ORGANISM: Pan troglodytes

<400> SEQUENCE: 5
ttgtagaatc tgcgaaggga catttgggag ctcattgagg cctatggtga aaaagcgaat      60
atccccagat aaaaactaga agaagctat ctgagaaact gctttgtgat gtgtgcattc     120
atctcacaga gttaaacctt tcttttgatt cagcagtttg gaaacactgt tt            172

<210> SEQ ID NO 6
<211> LENGTH: 171
<212> TYPE: DNA
<213> ORGANISM: Pan troglodytes
<220> FEATURE:
<221> NAME/KEY: misc_feature
<222> LOCATION: 45
<223> OTHER INFORMATION: n= a, t, g, c

<400> SEQUENCE: 6
ttgtggaatt tgcaagtgga gatttcaagc gctttgaggc caawnktaga aaaggaaata      60
tcttcgtata aaaactagac agaataattc tcagtaactt ctttgtgttg tgtgtattca     120
actcacagag ttgaaccttc ctttagacag agcagatttg aaacactctt t             171

<210> SEQ ID NO 7
<211> LENGTH: 171
<212> TYPE: DNA
<213> ORGANISM: Pan troglodytes

<400> SEQUENCE: 7
ttgtagaatc tgcaagtgga tatttggasc kctttgaggm cttcgktgga aacgggaata      60
tcttcacata aaaactagac agaagcattc tcagaaactt ctttgtgatg tttgcattca     120
actcacagag ttgaacmttc cttttgatag agcagttttg aaacactctt t             171

<210> SEQ ID NO 8
<211> LENGTH: 170
<212> TYPE: DNA
<213> ORGANISM: Pan troglodytes

<400> SEQUENCE: 8
ccattcgatt ccattcgatg attccattcg attccattcg atgatgattc cattcgattc      60
cattcgatga ttccattcga ttccattcga tgatgattcc attcgattcc attcgatgat     120
tccattcgat tccattcgat gatgattcca ttcgattcca ttcgatgatt               170
```